US006894149B2

(12) United States Patent
Tso et al.

(10) Patent No.: US 6,894,149 B2
(45) Date of Patent: May 17, 2005

(54) ANTI-HLA-DA ANTIBODIES AND THE METHODS OF USING THEREOF

(75) Inventors: J. Yun Tso, Menlo Park, CA (US); Jennifer McPhate Green, Belmont, CA (US)

(73) Assignee: Protein Design Labs, Inc., Fremont, CA (US)

( * ) Notice: Subject to any disclaimer, the term of this patent is extended or adjusted under 35 U.S.C. 154(b) by 0 days.

(21) Appl. No.: 10/268,883

(22) Filed: Oct. 10, 2002

(65) Prior Publication Data

US 2003/0138862 A1 Jul. 24, 2003

Related U.S. Application Data

(60) Provisional application No. 60/331,965, filed on Nov. 21, 2001, and provisional application No. 60/329,178, filed on Oct. 11, 2001.

(51) Int. Cl.⁷ .............................................. C07K 16/00

(52) U.S. Cl. .............................. 530/388.22; 530/387.3; 530/388.73; 530/388.8; 530/388.85; 530/391.7

(58) Field of Search ........................... 530/387.1, 387.3, 530/388.1, 388.22, 388.73, 388.8, 388.85, 391.7, 388.15; 424/133.1, 141.1, 143.1, 155.1, 183.1, 130.1, 134.1, 138.1, 142.1, 181.1

(56) References Cited

U.S. PATENT DOCUMENTS

| | | | |
|---|---|---|---|
| 5,004,692 A | 4/1991 | Tso et al. | |
| 5,301,101 A | 4/1994 | MacArthur et al. | |
| 5,552,530 A | 9/1996 | Johnson et al. | |
| 5,585,089 A | 12/1996 | Queen et al. | |
| 5,693,762 A | 12/1997 | Queen et al. | |
| 6,086,900 A | 7/2000 | Draper | |
| 6,129,914 A | 10/2000 | Weiner et al. | |
| 6,180,370 B1 | 1/2001 | Queen et al. | |
| 6,180,377 B1 | 1/2001 | Morgan et al. | |
| 6,416,958 B2 * | 7/2002 | Vidovic et al. | |
| 6,420,140 B1 | 7/2002 | Hori et al. | |

FOREIGN PATENT DOCUMENTS

| WO | WO 91/17271 | 6/1991 |
|---|---|---|
| WO | WO 91/10741 | 7/1991 |
| WO | WO 92/01047 | 10/1992 |
| WO | WO 93/12227 | 6/1993 |
| WO | WO 96/17874 | 6/1996 |
| WO | PCT/US02/32491 | 12/2003 |

OTHER PUBLICATIONS

Baldwin, et al., *Monoclonal Antibodies for Cancer Detection and Therapy*, Academic Press (1985).
Bird Robert E., et al., Single–Chain Antigen–Binding Proteins, *Science*, 242:423–6 (1988).
Brown, Eric J., "In Vitro Assays of Phagocytic Function of Human Peripheral Blood Leukocytes: Receptor Modulation and Signal Transduction", *Methods in Cell Biol.* 45:147 (1994).
Byers, Vera S., et al., "Rationale for Clinical Use of Immunotoxins in Cancer and Autoimmune Disease", *Seminars Cell Biol.* 2:59–70 (1991).
Demur, C., et al., "Effects of an Anti HLA–DR immunotoxin on Leukemic Cells and Hemopoietic Progenitors", *Leuk. Res.* 13(12):1047–54 (1989).
Fanger, Michael W., et al., "Bispecific Antibodies and Targeted Cellular Cytotoxicity", *Immunol. Today* 12:51–4 (1991).
Green, Jennifer M., et al., "Role of Cholesterol in Formation and Function of a Signaling Complex Involving Alphavβ3, Integrin–associated Protein (CD47), and Heterotrimeric G Proteins", *J. Cell Biol.* 146:673–82 (1999).
Greinix, H. T., et al., "Specific Growth Inhibition of Primative Hematopoietic Progenitor Cells Mediated Through Monoclonal Antibody Binding to MHC Class II Molecules", *Blood* 80(8):1950–1956 (1992).
Hajeer, A. H., et al., "Antibodies to Major Histocompatibility Complex Class II Inhibit Proliferation but Increase Production of Soluble CD23 in Lymphoblastoid B–Cell Lines", *Immunol.* 80(4):593–7 (1993).
Higaki, Y., et al., "Mechanisms Involved in the Inhibition of Growth of a Human B Lymphoma Cell Line, B104, by Anti–MHC Class II Antibodies", *Immunol. Cell Biol.* 72(3):205–14 (1994).
Hill, Mark, et al., "Exploration of Requirements for Peptide Binding to HLA DRB1*0101 and DRB1*0401", *J. Immunol.* 152, 2890–2898 (1994).
Hood et al., "Immunology", *Benjamin, N.Y., 2nd ed.* (1984).
Hu, Eddie, et al., "A Phase 1a Clinical Trial of LYM–1 Monoclonal Antibody Serotherapy in Patients with Refractory B Cell Malignancies", *Hematol. Oncol.* 7(2):155–66 (1989).
Hunkapiller, Tim, et al., "The Growing Immunoglobulin Gene Superfamily", *Nature*, 323:15–16 (1986).
Houston, et al., "Protein Engineering of Antibody Binding Sites: Recovery of Specific Activity in an Anti–Digoxin Single–Chain Fv Analogue Produced in *Escherichia Coli*", *Proc. Natl. Acad. Sci. U.S.A.*, 85:5879–83 (1988).
Kosteiny, et al., "Humanization and Characterization of the Anti–HLA–DR Antibody 1D10", *Int. J. Cancer* 93:(4):556–65 (2001).

(Continued)

Primary Examiner—Larry R. Helms
Assistant Examiner—David J. Blanchard
(74) Attorney, Agent, or Firm—Howrey Simon Arnold & White, LLP; Adam K. Whiting

(57) ABSTRACT

This invention provides anti-HLA-DR antibodies and the methods of use thereof for the treatment of leukemia or lymphomas, or solid tumors such as ovarian cancer or melanoma.

13 Claims, 14 Drawing Sheets

OTHER PUBLICATIONS

Lampson, et al., "Two Populations of Ia–Like Molecules on a Human B Cell Line", *Journal of Immunology*, 125(1): 293–99 (1980).

Landolfi, Nicholas F., et al., "Activated T–Lymphocytes Express Class I Molecules Which are Hyposialylated Compared to Other Lymphocyte Populations", *Molecular Immunol.* 23, 297–309 (1986).

Lanzavecchia A, et al., "The Use of Hybrid Hybridomas to Target Human Cytotoxic T–Lymphocytes", *Eur. J. Immunol.*, 17:105 (1987).

Mendelsohn, "Epidermal Growth Factor Receptor Inhibition by a Monoclonal Antibody as Anticancer Therapy", *Foundations of Clinical Cancer Research: Perspective for the $21^{st}$ Century*, 3(12) part 2 of 2 : 2703–07 (1997).

Miller, Chad G., "Adsorptive Biphasic Column Technology for Protein Sequence Analysis and Protein Chemical Modification", *Methods: A Companion to Methods in Enzymology* 6, 315–33 (1994).

Morgan, A., et al., "The N–Terminal End of the $C_H2$ Domain of Chimeric Human IgG1 Anti–HLA–DR is Necessay for C1q, FcyR1 and FcyR111 Binding", *Immunol.* 86(2):319–24 (1995).

Nagy, Zoltan A., et al., "Fully human, HLA–DR–Specific Monoclonal Antibodies Efficient Induce Programmed Death of Malignant Lymphoid Cells", *Nat Med.* 8(8):801–7 (2002).

Newell, M. Karen, et al., "Ligation of Major Histocompatibility Complex Class II Molecules Mediates Apoptotic Cell Death in Restin gB Lymphocytes", *Proc. Natl. Acad. Sci.* 90:10459–63 (1993).

O'Boyle, Kevin, et al., "Potentiation of Antiproliferative Effects of Monoclonal Antibody Lym1 and Immunoconjugate Lym–1–Gelonin on Human Burkitt's Lymphoma Cells with Gamma–Interferon and Tumor Necrosis Factor", *J. Immunother. Emphasis Tumor Immunol.* 18(4):221–30 (1995).

Olsnes, Sjur, et al., "Chimeric Toxins," *Pharmac. Ther.*, 15:355–81 (1982).

Ottonello, Luciano, et al., "Monoclonal Lym–1 Antibody–Dependent Lysis of B–Lymphoblastoid Tumor Targets by Human Complement and Cytokine–Exposed Mononuclear and Neutrophilic Polymorphonuclear Leukocytes", *Blood* 87(12):5171–8 (1996).

Pistillo, M. P.; et al., "Analysis of HLA Specificity of Human Monoclonal Antibodies by Cytofluorimetry and Cell ELISA", *Eur. J. Immunogenet* 18(5–6):345–53 (1991).

*Remiington's Pharmaceutical Science* (15th Ed., Mack Publishing Company, Easton, Pa., 1980).

Rose, L. M., et al., "Critical Lym–1 Binding Residues on Polymorphic Hla–DR Molecules", *Mol. Immunol.* 36(11–12);789–97 (1999).

Simons, K., et al., "Lipid Rafts and Signal Transduction", *Nature Reviews / Molecular Cell Biology.*, 1:31–9 (2000).

Truman, Jean–Philip, et al., "Lymphocute Programmed Cell Death is Mediated Via HLA Class II DR", *Int. Immunol.* 6(6):887–96 (1994).

Vidovic, Damir, et al., "Down–Regulation of Class II Major Histocompatibility Complex Molecules on Antigen–Presenting Cells by Antibody Fragments", *Eur. J. Immunol.* 25(12):3349–55 (1995).

Vidovic, D., et al., "Selective Apoptosis of Neoplastic Cells by the HLA–DR Specific Monoclonal Antibody", *Cancer Letters* 128:127–135 (1998).

Viken, Helge D., et al., "Serologic Subtyping of HLA–DR8 by Means of the Cytoxic Human Monoclonal Antibody 5643", *Hum. Immunol.* 43(3):200–6 (1995).

Würflein, Dieter, et al., "Evaluating Antibodies for Their Capacity to Induce Cell–mediated Lysis of Malignant B Cells", *Cancer Research* 58:3051–58(1998).

Dadmarz, et al., "Tumor–Infiltrating Lymphocytes from Human Ovarian Cancer Patients recognize Autologous tumor in an MHC Class II–Restricted Fashion," *Cancer J. Sci. Am.* 2(5):263 (1996) (abstract only).

Friedrich, et al., "Testing of acute myeloid leukemia of humans using monoclonal antibodies BL–DR, BL–M/G, BL–T2 and BL–IG–L/1," *Acta Histochem. Suppl.* 35:189–92 (1988) (abstract only).

Norose, et al., "Melanoma specific TH1 cytotoxic T Lymphocyte lines in Vogt–Koyanagi–Harada disease," *Br. J. Opthalmol.* 80(11): 1002–8 (1996) (abstract only).

Swanson, et al., "HLA–DR (Ia–like) reactivity in tumors of bone and soft tissue: an immunohistochemical comparison of monoclonal antibodies LN3 and LK8D3 in routinely processed specimens," *Mod. Pathol.* 3(2): 113–9 (1990) (abstract only).

Van Vreesswijk, et al., "Differential expression of HLA–DR, DQ, and DP antigens in primary and metastatic melanoma," *J. Invest. Dermatol.* 90(5): 755–60 (1998) (abstract only).

\* cited by examiner

Figure 2. Table 1.

| Clone # | AML KG-1 | AML THP-1 | Granulocyte | Stem Cell + | Lymphocyte | Monocyte | Apoptosis KG-1 | Apoptosis THP-1 | Antigen MW (kD) |
|---|---|---|---|---|---|---|---|---|---|
| K1-34 | +++ | ++ | +/- | +++ | ++ | + | + | +++ | 28/32 |
| K1-47 | +++ | ++ |  | ++ | +++ | ++ | ++ | +++ | 28/32 |
| K1-79 | +++ | ++ |  | ++ | +++ | +++ | + | ++ | 28/32 |
| K1-95 | +++ | +++ | +/- | ++ | ++ | + | + | + | 28/32 |
| K2-97 | +++ | ++ |  | +++ | +++ | +++ | + |  | 28/32 |
| K2-124 | +++ | ++ | +/- | +++ | +++ | +++ | + |  | 28/32 |
| K2-167 | ++ | +++ |  | +++ | +++ | +++ | + | +++ | 28/32 |
| K5-37 | +++ | +++ |  | +++ | +++ | +++ | + |  | 28/32 |
| K6-98 | +++ | +++ |  | +++ | +++ | +++ | ++ | +++ | 28/32 |
| K6-175 | ++ | ++ |  | + | + | + | +++ |  | 28/32 |
| K6-179 | +++ | +++ | +/- | ++ | +/- | + | ++ | +++ | 28/32 |
| K7-270 | +++ | +++ |  | ++ | ++ | ++ | ++ | +++ | 28/32 |
| K8-335 | +++ | ++ |  | ++ | +++ | +++ | +++ | +++ | 28/32 |
| K8-355 | +++ | +++ |  | ++ | +++ | +++ | +++ | ++ | 28/32 |
| K9-3 | ++ | +++ |  | +++ | ++ | ++ | ++ | +++ | 28/32 |
| K11-282 | +++ | ++ | ++ | ++ | +++ | +++ | + | +++ | 14 |
| K12-328 | ++ | + |  | ++ | + | + | +++ | NA | 40 |
| K9-64 | ++ | + |  | +++ | +++ | +++ | ++ |  | 32 |
| K11-230 | ++ | ++ |  | ++ | + | + |  | +++ | 180/80 |
| K2-109 | ++ | + |  | + | + | + | + | +++ | ND |
| K2-127 | ++ | + |  | ++ | + | + | + |  | ND |
| K5-71 | +++ |  |  | ++ | + | + |  |  | ND |
| K6-103 | +++ | ++ |  | + | ++ | + | ++ | NA | ND |
| K6-114 | ++ | + |  | + | +++ | + | ++ | ++ | ND |
| K6-121 | ++ | +++ |  | + | + | + | ++ | ++ | ND |
| K6-149 | +++ | ++ |  | +++ | ++ | ++ | + | +++ | ND |
| K6-150 | ++ | +++ |  | +++ | +++ | +++ | +++ | +++ | 30 |
| K7-196 | +++ | ++ |  | + | +++ | ++ | + | +++ | ND |
| K7-275 | ++ | +++ |  | ++ | + | + |  | +++ | ND |
| K8-343 | +++ | +++ |  | ++ | +++ | +++ | +++ | +++ | ND |
| K8-364 | ++ | + |  | + | ++ | + | +++ | +++ | ND |
| K8-365 | ++ | ++ |  | ++ | +++ | +++ | +++ | +++ | 38 |
| K9-92 | ++ | +++ |  | ++ | + | + | + | +++ | 80 |
| K11-272 | ++ | + | +/- | ++ | +++ | +++ | ++ | +++ | 97 |
| K11-280 | +++ | +++ | +/- | ++ | ++ | + | + | +++ | 80 |
| K12-360 | +++ | + |  | ++ | ++ | + | + | +++ | ND |

Figure 4:

K8-355 Heavy chain variable region cDNA sequence

```
                        30                              60
ATGGATTGGCTGTGGAACTTGCTATTCCTGATGGCAGCTGCCCAAAGTGCCCAAGCACAG
  M   D   W   L   W   N   L   L   F   L   M   A   A   A   Q   S   A   Q   A   Q 90                             120
ATCCAGTTGGTGCAGTCTGGACCTGAGCTGAAGAAGCCTGGAGAGACAGTCAAGATCTCC
  I   Q   L   V   Q   S   G   P   E   L   K   K   P   G   E   T   V   K   I   S 150                             180
TGCAAGGCTTCTAAATATACCTTCACAAACTATGGAATGAACTGGGTGAAGCAGGCTCCA
  C   K   A   S   K   Y   T   F   T   N   Y   G   M   N   W   V   K   Q   A   P 210                             240
GGAAAGGTTTTAAGGTGGATGGGCTGGATAAACACCTACACTGGAGAGCCAACATATGCT
  G   K   V   L   R   W   M   G   W   I   N   T   Y   T   G   E   P   T   Y   A 270                             300
GATGACTTCAAGGGACGATTTGCCTTCTCTTTGGAAACCTCTGCCAGCACTGCCTATTTG
  D   D   F   K   G   R   F   A   F   S   L   E   T   S   A   S   T   A   Y   L 330                             360
CAGATCAACAACCTCAAAAATGAGGACATGGCTACATATTTCTGTGCAACGACTACTTTG
  Q   I   N   N   L   K   N   E   D   M   A   T   Y   F   C   A   T   T   T   L 390                        414
ATTACTTACTACTTTGACTACTGGGGCCAAGGCACCACTCTCACAGTCTCCTCA
  I   T   Y   Y   F   D   Y   W   G   Q   G   T   T   L   T   V   S   S
```

Figure 5:

K8-355 Light chain variable region cDNA sequence

```
                              30                            60
ATGATGTCCTCTGCTCAGTTCCTTGGTCTCCTGTTGCTCTGTTTTCAAGGTACCAGATGT
 M   M   S   S   A   Q   F   L   G   L   L   L   L   C   F   Q   G   T   R   C 90                           120
GATATCCAGATGACACAGACTACATCCTCCCTGTCTGCCTCTCTGGGAGACAGAGTCACC
 D   I   Q   M   T   Q   T   T   S   S   L   S   A   S   L   G   D   R   V   T
 ‾

150                           180
ATCAGTTGCAGGTCAAGTCAGGACATTAGCAAATATTTAAACTGGTATCAGCAGAAACCA
 I   S   C   R   S   S   Q   D   I   S   K   Y   L   N   W   Y   Q   Q   K   P
             ‾‾‾ ‾‾‾ ‾‾‾ ‾‾‾ ‾‾‾ ‾‾‾ ‾‾‾ ‾‾‾ ‾‾‾ ‾‾‾ ‾‾‾

210                           240
GATGGAACTGTTAAACTCCTGATCTACTACACATCAAGATTACACTCAGGAGTCCCATCA
 D   G   T   V   K   L   L   I   Y   Y   T   S   R   L   H   S   G   V   P   S
                                 ‾‾‾ ‾‾‾ ‾‾‾ ‾‾‾ ‾‾‾ ‾‾‾ ‾‾‾

270                           300
AGGTTCAGTGGCAGTGGGTCTGGAACAGATTATTCTCTCACCATTAGCAACCTGGAGCAA
 R   F   S   G   S   G   S   G   T   D   Y   S   L   T   I   S   N   L   E   Q 330                           360
GAAGATATTGCCACTTACTTTTGCCAACAGGGTGATACGGTTCCTTGGACGTTCGGTGGA
 E   D   I   A   T   Y   F   C   Q   Q   G   D   T   V   P   W   T   F   G   G
                                 ‾‾‾ ‾‾‾ ‾‾‾ ‾‾‾ ‾‾‾ ‾‾‾ ‾‾‾ ‾‾‾ ‾‾‾

381
GGCACCAAGCTGGAAATCAAA
 G   T   K   L   E   I   K
```

Figure 7.

Table 2. Hybridoma screening for pan-HLA-DR antibodies. Spent media from 16 hybridomas were used to stain eight HLA-DR-expressing cell lines. Anti-HLA-DR antibodies, murine 1D10, L227, and L243 were used as controls.

| | #4 | #7 | #8 | #11 | #14 | #27 | #28 | #34 | #35 | #37 | #41 | #51 | #59 | #62 | #67 | #69 | 1D10 | L227 | L243 |
|---|---|---|---|---|---|---|---|---|---|---|---|---|---|---|---|---|---|---|---|
| Raji | +++ | +++ | +++ | ++ | ++ | +++ | ++ | ++ | +++ | +++ | +++ | +++ | +++ | +++ | +++ | +++ | +++ | +++ | +++ |
| Daudi | +++ | +++ | +++ | ++ | ++ | +++ | ++ | +++ | +++ | +++ | +++ | ++ | +++ | ++ | ++ | ++ | +/- | +++ | +++ |
| Ramos | +++ | +++ | ++ | ++ | - | ++ | ++ | ++ | +++ | +++ | ++ | +++ | +++ | - | - | - | ++ | +++ | +++ |
| Priess | +++ | +++ | +++ | ++ | ++ | +++ | +++ | +++ | +++ | +++ | +++ | ++ | +++ | +++ | +++ | ++ | +++ | +++ | +++ |
| CESS | +++ | +++ | +++ | ++ | ++ | +++ | +++ | +++ | +++ | +++ | +++ | ++ | +++ | ++ | ++ | - | - | +++ | +++ |
| RL | +++ | +++ | ++ | ++ | ++ | +++ | +++ | ++ | +++ | +++ | +++ | ++ | +++ | ++ | ++ | + | ++ | +++ | +++ |
| KG-1 | +++ | +++ | +++ | ++ | ++ | +++ | +++ | +++ | +++ | +++ | +++ | + | +++ | ND | ND | ND | ++ | +++ | +++ |

ND means not determined. "+++" indicates more than 2 log of mean channel fluorescence shift; "++", between 1.5-2 log shift; and +, 1 log shift. "-" means no binding

Figure 10

```
                          30                                60
ATGGATTGGCTGTGGAACTTGCTATTCCTGATGGCAGCTGCCCAAAGTGCCCAAGCACAG
 M  D  W  L  W  N  L  L  F  L  M  A  A  A  Q  S  A  Q  A  Q 90                               120
ATCCAGTTGGTGCAGTCTGGACCTGAGCTGAAGAAGCCTGGAGAGACAGTCAAGATCTCC
 I  Q  L  V  Q  S  G  P  E  L  K  K  P  G  E  T  V  K  I  S 150                               180
TGCAAGGCTTCTGGGTATACCTTCACAAACTATGGAATGAACTGGGTGAAGCAGGCTCCA
 C  K  A  S  G  Y  T  F  T  N  Y  G  M  N  W  V  K  Q  A  P 210                               240
GGAAAGGGTTTAAAGTGGATGGCCTGGATAAACACCTACAATGGAGAGCCAACATATGCT
 G  K  G  L  K  W  M  A  W  I  N  T  Y  N  G  E  P  T  Y  A 270                               300
GATGACTTCAAGGGACGGTTTGCCTTCTCTTTGGAAACCTCTGCCAGAACTGCCTATTTG
 D  D  F  K  G  R  F  A  F  S  L  E  T  S  A  R  T  A  Y  L 330                               360
CAGATCAACAACCTCAAAAATGAGGACATGGCTACATATTTCTGTGCAAGAGGGGATTAC
 Q  I  N  N  L  K  N  E  D  M  A  T  Y  F  C  A  R  G  D  Y 390                      411
TACGGCCCTTTTGACTACTGGGGCCAAGGCACCACTCTCACAGTCTCCTCA
 Y  G  P  F  D  Y  W  G  Q  G  T  T  L  T  V  S  S
```

Figure 11

```
                                30                                    60
ATGGACATGAGGGTTCCTGCTCACGTTTTTGGCTTCTTGTTGCTCTGGTTTCCAGGTACC
 M   D   M   R   V   P   A   H   V   F   G   F   L   L   W   F   P   G   T 90                                   120
AGATGTGACATCCAGATGACCCAGTCTCCATCCTCCTTATCTGCCTCTCTGGGAGAAAGA
 R   C   D   I   Q   M   T   Q   S   P   S   S   L   S   A   S   L   G   E   R 150                                   180
GTCAGTCTCACTTGTCGGGCAAGTCAGGAAATTAGTGGTTACTTAAGCTGGCTTCAGCAG
 V   S   L   T   C   R   A   S   Q   E   I   S   G   Y   L   S   W   L   Q   Q 210                                   240
AAACCAGATGGAACTATTAAACGCCTGATCTACGCCGCATCCACTTTAGATTCTGGTGTC
 K   P   D   G   T   I   K   R   L   I   Y   A   A   S   T   L   D   S   G   V 270                                   300
CCAAAAAGGTTCAGTGGCAGTAGGTCTGGGTCAGATTATTCTCTCACCATCAGCAGCCTT
 P   K   R   F   S   G   S   R   S   G   S   D   Y   S   L   T   I   S   S   L 330                                   360
GAGTCTGAAGATTTTGCAGACTATTACTGTCTACAATATGTTAGTTATCCTCGGACGTTC
 E   S   E   D   F   A   D   Y   Y   C   L   Q   Y   V   S   Y   P   R   T   F

390
GGTGGAGGCACCAAGCTGGAAATCAAACGG
 G   G   G   T   K   L   E   I   K   R
```

Figure 12.

Table 3. Reactivity of Pan-HLA-DR antibodies to four types of solid tumor cell lines.

| Cell line | Cancer type | 1D10 | L227 | Anti-HLA-DR #4 | K8-355 |
|---|---|---|---|---|---|
| PC-3 | Prostate | - | - | - | - |
| LNCaP | Prostate | - | - | - | - |
| 22RV1 | Prostate | - | - | - | - |
| DU145 | Prostate | - | - | - | - |
| OVCAR-5 | Ovarian | -/+ | -/+ | +/+++ | +/++ |
| OVCAR-3 | Ovarian | - | - | - | - |
| OVCAR-8 | Ovarian | - | - | - | - |
| OVCAR-4 | Ovarian | - | - | - | - |
| SK-OV-3 | Ovarian | - | - | - | - |
| IGROV-1 | Ovarian | - | - | - | - |
| SW626 | Ovarian | -/+ | -/+ | -/++ | -/+ |
| Caov-3 | Ovarian | - | - | - | - |
| ASPC-1 | Pancreatic | - | - | - | - |
| BXPC-3 | Pancreatic | - | - | - | - |
| C32 | Melanoma | ++ | ++ | +++ | ++ |
| HT-144 | Melanoma | ++ | ++ | ++ | +++ |
| SK-MEL-28 | Melanoma | -/+ | -/+ | -/+ | -/+ |
| M14 | Melanoma | -/+ | -/++ | -/++ | -/+ |
| A2058 | Melanoma | - | - | - | - |
| CHL-1 | Melanoma | - | - | - | - |

"-" means no binding. "+++" indicates more than 2 log of mean channel fluorescence shift; "++", between 1.5-2 log shift; and +, 1 log shift. "-/+" means reactivity ranges from bo binding to 1.5-2 log shift.

Figure 14
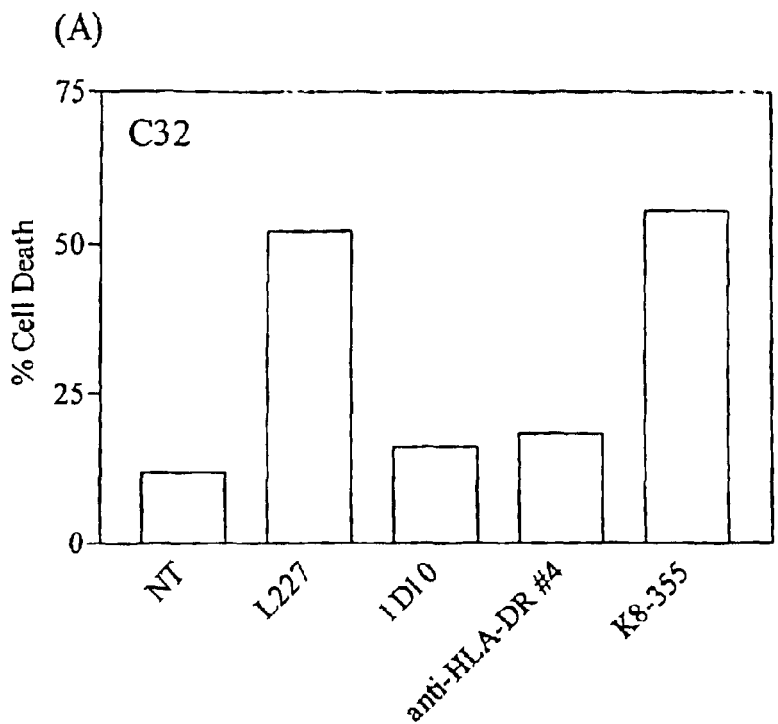
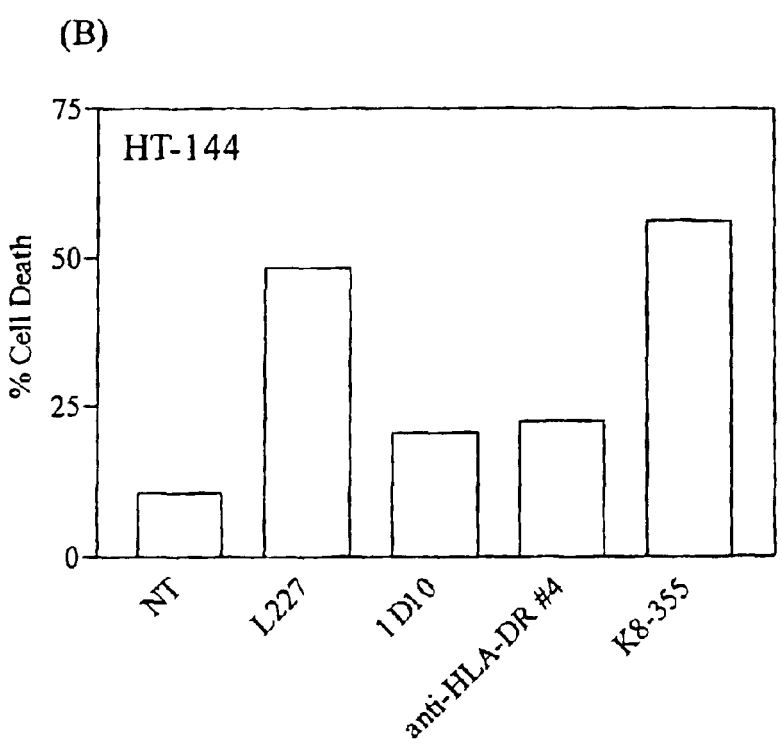

SEQUENCE LISTING

<160> NUMBER OF SEQ ID NOS: 16

<210> SEQ ID NO 1
<211> LENGTH: 414
<212> TYPE: DNA
<213> ORGANISM: Mouse

<400> SEQUENCE: 1

-continued

| | |
|---|---|
| atggattggc tgtggaactt gctattcctg atggcagctg cccaaagtgc ccaagcacag | 60 |
| atccagttgg tgcagtctgg acctgagctg aagaagcctg gagagacagt caagatctcc | 120 |
| tgcaaggctt ctaaatatac cttcacaaac tatggaatga actgggtgaa gcaggctcca | 180 |
| ggaaaggttt taaggtggat gggctggata acacctaca ctggagagcc aacatatgct | 240 |
| gatgacttca aggacgatt tgccttctct ttggaaacct ctgccagcac tgcctatttg | 300 |
| cagatcaaca acctcaaaaa tgaggacatg gctacatatt tctgtgcaac gactactttg | 360 |
| attacttact actttgacta ctggggccaa ggcaccactc tcacagtctc ctca | 414 |

<210> SEQ ID NO 2
<211> LENGTH: 138
<212> TYPE: PRT
<213> ORGANISM: Mouse

<400> SEQUENCE: 2

```
Met Asp Trp Leu Trp Asn Leu Leu Phe Leu Met Ala Ala Ala Gln Ser
1               5                   10                  15

Ala Gln Ala Gln Ile Gln Leu Val Gln Ser Gly Pro Glu Leu Lys Lys
            20                  25                  30

Pro Gly Glu Thr Val Lys Ile Ser Cys Lys Ala Ser Lys Tyr Thr Phe
        35                  40                  45

Thr Asn Tyr Gly Met Asn Trp Val Lys Gln Ala Pro Gly Lys Val Leu
    50                  55                  60

Arg Trp Met Gly Trp Ile Asn Thr Tyr Thr Gly Glu Pro Thr Tyr Ala
65                  70                  75                  80

Asp Asp Phe Lys Gly Arg Phe Ala Phe Ser Leu Glu Thr Ser Ala Ser
                85                  90                  95

Thr Ala Tyr Leu Gln Ile Asn Asn Leu Lys Asn Glu Asp Met Ala Thr
            100                 105                 110

Tyr Phe Cys Ala Thr Thr Thr Leu Ile Thr Tyr Tyr Phe Asp Tyr Trp
        115                 120                 125

Gly Gln Gly Thr Thr Leu Thr Val Ser Ser
    130                 135
```

<210> SEQ ID NO 3
<211> LENGTH: 119
<212> TYPE: PRT
<213> ORGANISM: Mouse

<400> SEQUENCE: 3

```
Gln Ile Gln Leu Val Gln Ser Gly Pro Glu Leu Lys Lys Pro Gly Glu
1               5                   10                  15

Thr Val Lys Ile Ser Cys Lys Ala Ser Lys Tyr Thr Phe Thr Asn Tyr
            20                  25                  30

Gly Met Asn Trp Val Lys Gln Ala Pro Gly Lys Val Leu Arg Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Met Ala Thr Tyr Phe Cys
                85                  90                  95

Ala Thr Thr Thr Leu Ile Thr Tyr Tyr Phe Asp Tyr Trp Gly Gln Gly
            100                 105                 110

Thr Thr Leu Thr Val Ser Ser
```

-continued

```
                115
```

<210> SEQ ID NO 4
<211> LENGTH: 381
<212> TYPE: DNA
<213> ORGANISM: Mouse

<400> SEQUENCE: 4

| | |
|---|---|
| atgatgtcct ctgctcagtt ccttggtctc ctgttgctct gttttcaagg taccagatgt | 60 |
| gatatccaga tgacacagac tacatcctcc ctgtctgcct ctctgggaga cagagtcacc | 120 |
| atcagttgca ggtcaagtca ggacattagc aaatatttaa actggtatca gcagaaacca | 180 |
| gatggaactg ttaaactcct gatctactac acatcaagat tacactcagg agtcccatca | 240 |
| aggttcagtg gcagtgggtc tggaacagat tattctctca ccattagcaa cctggagcaa | 300 |
| gaagatattg ccacttactt ttgccaacag ggtgatacgg ttccttggac gttcggtgga | 360 |
| ggcaccaagc tggaaatcaa a | 381 |

<210> SEQ ID NO 5
<211> LENGTH: 127
<212> TYPE: PRT
<213> ORGANISM: Mouse

<400> SEQUENCE: 5

Met Met Ser Ser Ala Gln Phe Leu Gly Leu Leu Leu Cys Phe Gln
1               5                   10                  15

Gly Thr Arg Cys Asp Ile Gln Met Thr Gln Thr Thr Ser Ser Leu Ser
            20                  25                  30

Ala Ser Leu Gly Asp Arg Val Thr Ile Ser Cys Arg Ser Ser Gln Asp
        35                  40                  45

Ile Ser Lys Tyr Leu Asn Trp Tyr Gln Gln Lys Pro Asp Gly Thr Val
    50                  55                  60

Lys Leu Leu Ile Tyr Tyr Thr Ser Arg Leu His Ser Gly Val Pro Ser
65                  70                  75                  80

Arg Phe Ser Gly Ser Gly Ser Gly Thr Asp Tyr Ser Leu Thr Ile Ser
                85                  90                  95

Asn Leu Glu Gln Glu Asp Ile Ala Thr Tyr Phe Cys Gln Gln Gly Asp
            100                 105                 110

Thr Val Pro Trp Thr Phe Gly Gly Gly Thr Lys Leu Glu Ile Lys
        115                 120                 125

<210> SEQ ID NO 6
<211> LENGTH: 107
<212> TYPE: PRT
<213> ORGANISM: Mouse

<400> SEQUENCE: 6

Asp Ile Gln Met Thr Gln Thr Thr Ser Ser Leu Ser Ala Ser Leu Gly
1               5                   10                  15

Asp Arg Val Thr Ile Ser Cys Arg Ser Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

```
Glu Asp Ile Ala Thr Tyr Phe Cys Gln Gln Gly Asp Thr Val Pro Trp
                85                  90                  95
Thr Phe Gly Gly Gly Thr Lys Leu Glu Ile Lys
            100                 105

<210> SEQ ID NO 7
<211> LENGTH: 411
<212> TYPE: DNA
<213> ORGANISM: Mouse

<400> SEQUENCE: 7
atggattggc tgtggaactt gctattcctg atggcagctg cccaaagtgc ccaagcacag      60
atccagttgg tgcagtctgg acctgagctg aagaagcctg agagacagt caagatctcc     120 tgcaaggctt ctgggtatac cttcacaaac tatggaatga actgggtgaa gcaggctcca    180
ggaaagggtt taaagtggat ggcctggata acacctaca atggagagcc aacatatgct     240
gatgacttca aggacggtt tgccttctct ttggaaacct ctgccagaac tgcctatttg     300
cagatcaaca acctcaaaaa tgaggacatg gctacatatt tctgtgcaag aggggattac    360
tacggccctt ttgactactg gggccaaggc accactctca cagtctcctc a             411

<210> SEQ ID NO 8
<211> LENGTH: 137
<212> TYPE: PRT
<213> ORGANISM: Mouse

<400> SEQUENCE: 8

Met Asp Trp Leu Trp Asn Leu Leu Phe Leu Met Ala Ala Ala Gln Ser
1               5                   10                  15

Ala Gln Ala Gln Ile Gln Leu Val Gln Ser Gly Pro Glu Leu Lys Lys
            20                  25                  30

Pro Gly Glu Thr Val Lys Ile Ser Cys Lys Ala Ser Gly Tyr Thr Phe
        35                  40                  45

Thr Asn Tyr Gly Met Asn Trp Val Lys Gln Ala Pro Gly Lys Gly Leu
    50                  55                  60

Lys Trp Met Ala Trp Ile Asn Thr Tyr Asn Gly Glu Pro Thr Tyr Ala
65                  70                  75                  80

Asp Asp Phe Lys Gly Arg Phe Ala Phe Ser Leu Glu Thr Ser Ala Arg
                85                  90                  95

Thr Ala Tyr Leu Gln Ile Asn Asn Leu Lys Asn Glu Asp Met Ala Thr
            100                 105                 110

Tyr Phe Cys Ala Arg Gly Asp Tyr Tyr Gly Pro Phe Asp Tyr Trp Gly
        115                 120                 125

Gln Gly Thr Thr Leu Thr Val Ser Ser
    130                 135

<210> SEQ ID NO 9
<211> LENGTH: 118
<212> TYPE: PRT
<213> ORGANISM: Mouse

<400> SEQUENCE: 9

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45
```

Ala Trp Ile Asn Thr Tyr Asn Gly Glu Pro Thr Tyr Ala Asp Asp Phe
            50                  55                  60

Lys Gly Arg Phe Ala Phe Ser Leu Glu Thr Ser Ala Arg Thr Ala Tyr
 65                  70                  75                  80

Leu Gln Ile Asn Asn Leu Lys Asn Glu Asp Met Ala Thr Tyr Phe Cys
                85                  90                  95

Ala Arg Gly Asp Tyr Tyr Gly Pro Phe Asp Tyr Trp Gly Gln Gly Thr
            100                 105                 110

Thr Leu Thr Val Ser Ser
        115

<210> SEQ ID NO 10
<211> LENGTH: 390
<212> TYPE: DNA
<213> ORGANISM: Mouse

<400> SEQUENCE: 10
atggacatga gggttcctgc tcacgttttt ggcttcttgt tgctctggtt tccaggtacc    60
agatgtgaca tccagatgac ccagtctcca tcctccttat ctgcctctct gggagaaaga   120
gtcagtctca cttgtcgggc aagtcaggaa attagtggtt acttaagctg gcttcagcag   180
aaaccagatg gaactattaa acgcctgatc tacgccgcat ccactttaga ttctggtgtc   240
ccaaaaaggt tcagtggcag taggtctggg tcagattatt ctctcaccat cagcagcctt   300
gagtctgaag attttgcaga ctattactgt ctacaatatg ttagttatcc tcggacgttc   360
ggtggaggca ccaagctgga aatcaaacgg                                    390

<210> SEQ ID NO 11
<211> LENGTH: 130
<212> TYPE: PRT
<213> ORGANISM: Mouse

<400> SEQUENCE: 11

Met Asp Met Arg Val Pro Ala His Val Phe Gly Phe Leu Leu Leu Trp
 1               5                  10                  15

Phe Pro Gly Thr Arg Cys Asp Ile Gln Met Thr Gln Ser Pro Ser Ser
                20                  25                  30

Leu Ser Ala Ser Leu Gly Glu Arg Val Ser Leu Thr Cys Arg Ala Ser
            35                  40                  45

Gln Glu Ile Ser Gly Tyr Leu Ser Trp Leu Gln Gln Lys Pro Asp Gly
 50                  55                  60

Thr Ile Lys Arg Leu Ile Tyr Ala Ala Ser Thr Leu Asp Ser Gly Val
 65                  70                  75                  80

Pro Lys Arg Phe Ser Gly Ser Arg Ser Gly Ser Asp Tyr Ser Leu Thr
                85                  90                  95

Ile Ser Ser Leu Glu Ser Glu Asp Phe Ala Asp Tyr Tyr Cys Leu Gln
            100                 105                 110

Tyr Val Ser Tyr Pro Arg Thr Phe Gly Gly Gly Thr Lys Leu Glu Ile
        115                 120                 125

Lys Arg
    130

<210> SEQ ID NO 12
<211> LENGTH: 108
<212> TYPE: PRT
<213> ORGANISM: Mouse

-continued

```
<400> SEQUENCE: 12

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Glu Ile Ser Gly Tyr
            20                  25                  30

Leu Ser Trp Leu Gln Gln Lys Pro Asp Gly Thr Ile Lys Arg Leu Ile
        35                  40                  45

Tyr Ala Ala Ser Thr Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Val Ser Tyr Pro Arg
                85                  90                  95

Thr Phe Gly Gly Gly Thr Lys Leu Glu Ile Lys Arg
            100                 105

<210> SEQ ID NO 13
<211> LENGTH: 21
<212> TYPE: DNA
<213> ORGANISM: Artificial Sequence
<220> FEATURE:
<223> OTHER INFORMATION: Synthetic

<400> SEQUENCE: 13
gatggataca gttggtgcag c                                         21

<210> SEQ ID NO 14
<211> LENGTH: 20
<212> TYPE: DNA
<213> ORGANISM: Artificial Sequence
<220> FEATURE:
<223> OTHER INFORMATION: Synthetic

<400> SEQUENCE: 14
gccagtggat agacagatgg                                           20

<210> SEQ ID NO 15
<211> LENGTH: 46
<212> TYPE: DNA
<213> ORGANISM: Artificial Sequence
<220> FEATURE:
<223> OTHER INFORMATION: Synthetic

<400> SEQUENCE: 15
tatagagctc aagcttggat ggtgggaaga tggatacagt tggtgc               46

<210> SEQ ID NO 16
<211> LENGTH: 54
<212> TYPE: DNA
<213> ORGANISM: Artificial Sequence
<220> FEATURE:
<223> OTHER INFORMATION: Synthetic

<400> SEQUENCE: 16
tatagagctc aagcttccag tggatagaca ctgatggggg ctgtctgttt tggc      54
```

ANTI-HLA-DA ANTIBODIES AND THE METHODS OF USING THEREOF

This application claims the benefit of priority of the U.S. provisional application Ser. No. 60/329,178 filed Oct. 11, 2001 and the U.S. provisional application Ser. No. 60/331,965, filed Nov. 21, 2001, each of which is incorporated by reference in its entirety.

FIELD OF THE INVENTION

This invention concerns anti-HLA-DR antibodies and the methods of using thereof for the treatment of leukemia, lymphoma or solid tumor

BACKGROUND OF THE INVENTION

The leukemias are a heterogeneous group of neoplasm arising from the malignant transformation of hematopoietic (blood forming) cells. Leukemic cells proliferate primarily in bone marrow and lymphoid tissues where they interfere with normal hematopoiesis and immunity. Ultimately, they emigrate into the peripheral blood and infiltrate other tissues.

Leukemias are classified according to the cell types primarily involved (myloid and lymphoid) and as acute or chronic based upon the natural history of the disease. Acute leukemias, including acute lymphocytic leukemia (ALL) and acute myelogenous leukemia (AML), have a rapid clinical course and often result in death within a matter of months without effective treatment. In contrast, chronic leukemias have a more prolonged natural history. Chronic leukemias include chronic lymphocytic leukemia (CCL), chronic myelogenous leukemia (CML) and hairy cell leukemia.

It is of great significance to develop new and effective drugs for the treatment of leukemia. The present invention provides an anti-HLA-DR antibodies and the method of use thereof for treating leukemia, lymphoma or solid tumor.

U.S. Pat. No. 6,416,958 discloses anti-human major histocompatibility complex (MHC) class II, HLA-DR-specific antibodies, which can induce apoptosis of HLA-DR positive cells. However, the '958 patent does not disclose the anti-HLA-DR antibodies that bind to and induce apoptosis of solid tumor cells in the present invention.

U.S. Pat. No. 6,129,914 discloses 1D10 antibodies that specifically bind to malignant B-cells. However, the '914 patent does not disclose the antibody of the present invention, which is a pan anti-HLA-DR, binding to CESS (myelomonocytic leukemia, American Type Culture Collection (ATCC)), Daudi (Burkitts lymphoma, ATCC), KG-1 (acute myelocytic leukemia, ATCC), Raji (Burkitt's lymphoma, ATCC), Ramos (Burkitt's lymphoma, ATCC), RL (non-Hodgkin's lymphoma, ATCC), THP-1 (acute myclocytic leukemia, ATCC), OVCAR-5 (ovarian cancer, ATCC), C32 (melanoma, ATCC), and HT-144 (ATCC).

The present invention provides anti-HLA-DR antibodies. Such antibodies induce apoptosis of various types of lymphoma cells, leukemia cells, preferably AML cells, or Burkitts lymphoma cells, and some solid tumor cells, preferably ovarian or melanoma cancer cells. The anti-HLA-DR antibodies can be used for the treatment of leukemia, lymphoma or solid tumor.

SUMMARY OF THE INVENTION

The present invention provides an anti-HLA-DR antibody that binds to solid tumor cells such as ovarian tumor cells and melanoma cells as well as various types of leukemia or lymphoma cells and the method of using thereof for the treatment or detection of leukemia, lymphoma or solid tumors.

DESCRIPTION OF THE DRAWINGS

FIG. 2. Table 1 shows the reactivity profiles of 36 anti-KG-1 lipid raft hybridomas that showed apoptosis-inducing activity.

FIG. 4. Nucleotide sequence and deduced amino acid sequence of the heavy chain variable region (VH) of K8-355 (anti-HLA-DR) (SEQ ID Nos: 1 and 2), The signal peptide is in italic, the three complementarity determining regions (CDRs) are underlined, and the first NH2-terminal amino acid residue of the matured heavy chain (Mouse IgG1) is in bold. SEQ ID NO: 3 depicts the amino acid sequence of the heavy chain variable region (VH) of K8-355 (anti-HLA-DR) (signal peptide is not included, SEQ ID NO:3 includes the amino acid sequence starting from position 20 of SEQ ID NO:2).

FIG. 5. Nucleotide sequence and deduced amino acid sequence of the light chain variable region (VL) of K8-355 (anti-HLA-DR) (SEQ ID Nos: 4 and 5). The signal peptide is in italic, the three complementarity determining regions (CDRs) are underlined, and the first NH2-terminal amino acid residue of the matured light chain (mouse kappa) is in bold. SEQ ID NO: 6 is the amino acid sequence of the light chain variable region (VL) of K8-355 (anti-HLA-DR) (signal peptide is not included, SEQ ID NO:6 includes the amino acid sequence starting from position 21 of SEQ ID NO:5).

FIG. 7. Table 2. Hybridoma screening for pan-HLA-DR antibodies.

FIG. 10. Nucleotide sequence and deduced amino acid sequence of the heavy chain variable region (VH) of anti-HLA-DR #4 (SEQ ID Nos: 7 and 8). The signal peptide is in italic, the three complementarity determining regions (CDRs) are underlined, and the first NH2-terminal amino acid residue of the matured heavy chain (Mouse IgG1) is in bold. SEQ ID NO: 9 depicts the amino acid sequence of the heavy chain variable region (VH) of anti-HLA-DR #4 (anti-HLA-DR) (signal peptide is not included, SEQ ID NO:9 includes the amino acid sequence starting from position 20 of SEQ ID NO:8).

FIG. 11. Nucleotide sequence and deduced amino acid sequence of the light chain variable region (VL) of anti-HLA-DR #4 (SEQ ID Nos: 10 and 11). The signal peptide is in italic, the three complementarity determining regions (CDRs) are underlined, and the first NH2-terminal amino acid residue of the matured light chain (mouse kappa) is in bold. SEQ ID NO: 12 depicts the amino acid sequence of the light chain variable region (VL) of anti-HLA-DR #4 (anti-HLA-DR) (signal peptide is not included, SEQ ID NO:12 includes the amino acid sequence starting from position 23 of SEQ ID NO:11).

FIG. 12. Table 3. Reactivity of anti-HLA-DR antibodies to four types of solid tumor cell lines.

FIG. 14. Apoptosis of (A) C32 melanoma cells and (B) HT-144 melanoma cells induced by anti-HLA-DR antibodies. Experimental conditions were described in the "Material and Methods" section using purified antibodies.

DETAILED DESCRIPTION OF THE PREFERRED EMBODIMENTS

Figure 1:
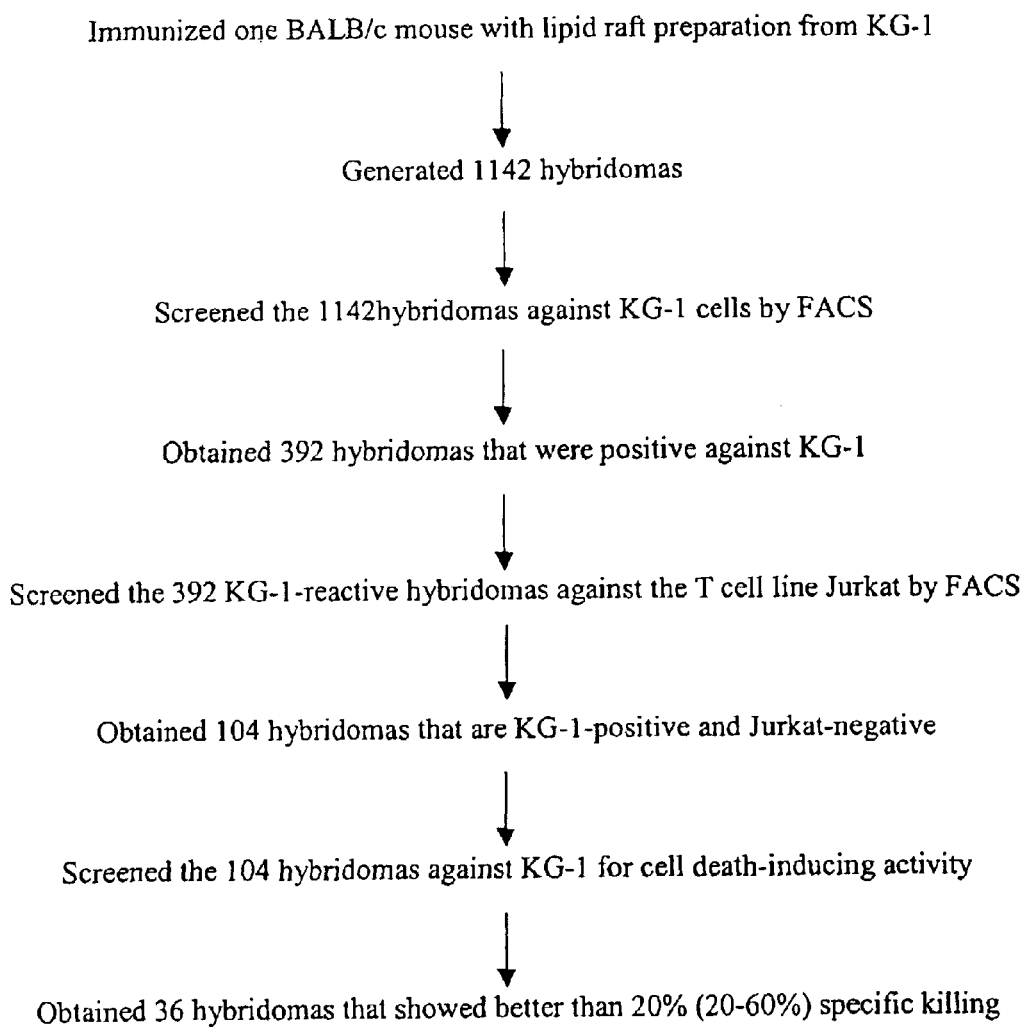
FIG. 1. Flow chart summarizing how the tumor-specific hybridomas were obtained from the KG-1 lipid raft immunization.

As used herein, the term "antibody" or "immunoglobulin" refers to a protein consisting of one or more polypeptides substantially encoded by immunoglobulin genes. The recognized immunoglobulin genes include the kappa, lambda, alpha, gamma ($IgG_1$, $IgG_2$, $IgG_3$, $IgG_4$), delta, epsilon and mu constant region genes, as well as the myriad immunoglobulin variable region genes. Full-length immunoglobulin "light chains" (about 25 Kd or 214 amino acids) are encoded by a variable region gene at the NH2-terminus (about 110 amino acids) and a kappa or lambda constant region gene at the COOH-terminus. Full-length immunoglobulin "heavy chains" (about 50 Kd or 446 amino acids), are similarly encoded by a variable region gene (about 116 amino acids) and one of the other aforementioned constant region genes, e.g., gamma (encoding about 330 amino acids).

One form of immunoglobulin constitutes the basic structural unit of an antibody. This form is a tetramer and consists of two identical pairs of immunoglobulin chains, each pair having one light and one heavy chain. In each pair, the light and heavy chain variable regions are together responsible for binding to an antigen, and the constant regions are responsible for the antibody effector functions. In addition to antibodies, immunoglobulins may exist in a variety of other forms including, for example, Fv, Fab, and (Fab')$_2$, as well as bifunctional hybrid antibodies (e.g., Lanzavecchia et al., Eur. J. Immunol. 17, 105 (1987)) and in single chains (e.g., Huston et al., Proc. Natl. Acad. Sci. U.S.A., 85, 5879–5883 (1988) and Bird et al., Science, 242, 423–426 (1988), which are incorporated herein by reference). (See, generally, Hood et al., "Immunology", Benjamin, N.Y., 2nd ed. (1984), and Hunkapiller and Hood, Nature, 323, 15–16 (1986), which are incorporated herein by reference).

The term "genetically altered antibodies" means antibodies wherein the amino acid sequence has been varied from that of a native antibody. Because of the relevance of recombinant DNA techniques to this invention, one need not be confined to the sequences of amino acids found in natural antibodies; antibodies can be redesigned to obtain desired characteristics. The possible variations are many and range from the changing of just one or a few amino acids to the complete redesign of, for example, the variable or constant region. Changes in the constant region will, in general, be made in order to improve or alter characteristics, such as complement fixation, interaction with membranes and other effector functions. Changes in the variable region will be made in order to improve the antigen binding characteristics.

The term "humanized antibody" or "humanized immunoglobulin" refers to an immunoglobulin comprising a human framework, at least one and preferably all complimentarity determining regions (CDRs) from a non-human antibody, and in which any constant region present is substantially identical to a human immunoglobulin constant region, i.e., at least about 85–90%, preferably at least 95% identical. Hence, all parts of a humanized immunoglobulin, except possibly the CDRs, are substantially identical to corresponding parts of one or more native human immunoglobulin sequences. See, e.g. Queen et al., U.S. Pat. Nos. 5,5301,101; 5,585,089; 5,693,762; and 6,180,370 (each of which is incorporated by reference in its entirety).

The term "chimeric antibody" refers to an antibody in which the constant region comes from an antibody of one species (typically human) and the variable region comes from an antibody of another species (typically rodent).

The term "apoptosis", "apoptotic cell death" or "programmed cell death" as used herein refers to any cell death that results from the complex cascade of cellular events that occur at specific stages of cellular differentiation and in response to specific stimuli. Apoptotic cell death is characterized by condensation of the cytoplasm and nucleus of dying cells.

By "a pharmaceutically effective" amount of a drug or pharmacologically active agent or pharmaceutical formulation is meant a nontoxic but sufficient amount of the drug, agent or formulation to provide the desired effect.

A "subject," "individual" or "patient" is used interchangeably herein, which refers to a vertebrate, preferably a mammal, more preferably a human.

The term "derived from" means "descending from", "obtained from" or "produced by".

The term "lipid raft" refers to a lipid raft or a portion thereof in a clustered state or a non-clustered state, including "lipid raft", "clustered lipid rafts", and "DRM", each of which has been described in detail in Simons, K., et al., Nature Reviews/Molecular Cell Biology: Vol. 1 pp 31–39 (2000). In particular, "lipid raft" contains a given set of proteins that can change size and composition in response to intra- or extracellular stimuli. This favors specific protein-protein interactions, resulting in the activation of signally cascade. Sometimes, the lipid rafts may be clustered together. It has been reported that clustering is used both artificially and physiologically to trigger signally cascades. DRMs (detergent-resistant membranes) are the rafts that remain insoluble after treatment on ice with detergents, such as Triton X-100 or NP-40. They are believed to be non-native aggregated rafts.

The present invention provides for antibodies that bind to or neutralizes HLA-DR. The antibodies may be in polyclonal or monoclonal form and may bind to any one or more epitope or subunit of HLA-DR. Anti-HLA-DR antibodies of all species and origins are included. Non-limiting exemplary antibodies include anti-HLA-DR antibodies derived from human, chicken, goats, and rodents (e.g., rats, mice, hamsters and rabbits), including transgenic rodents genetically engineered to produce human antibodies (see, e.g., Lonberg et al., WO93/12227 (1993) and Kucherlapati, et al., WO91/10741 (1991)), which are herein incorporated by reference in their entirety). Antibodies useful in the present invention also may be made using phage display methods (see, e.g., Dower et al., WO91/17271 and McCafferty et al., WO92/01047, which are herein incorporated by reference in their entirety).

The anti-HLA-DR antibodies of the present invention bind to the cells derived from a solid tumor, including but not limited to, ovarian tumor or melanoma. Preferably, the antibody binds to both ovarian tumor (cancer) cells and melanoma cells. The ovarian tumor cells are derived from OVCAR-5 cell line, while the melanoma cells are derived from cells of C32 cell line.

The antibodies of the present invention also bind to cells selected from the group consisting of myelomonocytic leukemia cells, Burkitts lymphoma cells, acute myelocytic leukemia cells, and non-Hodgkin's lymphoma cells.

Preferably, the anti-HLA-DR antibody binds to cells selected from the group consisting of CESS (myelomonocytic leukemia, American Type Culture Collection (ATCC)), Daudi (Burkitts lymphoma, ATCC), KG-1 (acute myelocytic leukemia, ATCC), Raji (Burkitt's lymphoma, ATCC), Ramos (Burkitt's lymphoma, ATCC), RL (non-Hodgkin's lymphoma, ATCC), THP-1 (acute myelocytic leukemia, ATCC), OVCAR-5 (ovarian cancer, ATCC), and C32 (melanoma, ATCC, HT-144, ATCC).

More preferably, the antibodies bind to myelomonocytic leukemia cells, Burkitts lymphoma cells, acute myelocytic leukemia cells, non-Hodgkin's lymphoma cells, ovarian tumor (cancer) cells, and melanoma cells.

Some of the anti-HLA-DR antibodies of the present invention also bind to an isolated lipid raft. Preferably, the isolated lipid raft is derived from cancer cells, and more preferably from acute myelocytic leukemia cells. Since the HLA-DR antigen is associated with lipid rafts of cancer cells. Immunization of a host animal, for example, mouse, with the lipid rafts obtained from leukemia cells gives rise to hybridoma antibodies that bind to HLA-DR as well as the lipid rafts. These hybridoma antibodies include, but are not limited to, K8-355.

In one aspect of the present invention, the anti-HLA-DR antibodies of the present invention comprise a heavy chain variable region having an amino acid sequence of SEQ ID NO: 3. The antibodies may further comprise a light chain variable region having an amino acid sequence of SEQ ID NO: 6. Preferably, the antibody is K8-355.

In another aspect of the present invention, the anti-HLA-DR antibodies comprise a heavy chain variable region having an amino acid sequence of SEQ ID NO: 9. The antibodies further comprise a light chain variable region having an amino acid sequence of SEQ ID NO: 12. Preferably, the antibody is anti-HLA-DR #4.

The constant regions of the antibodies can be all types of constant regions, including IgM, IgG, IgD, IgA and IgE, and any isotype, including IgG1,IgG2, IgG3 and IgG4. The light chain of the antibody can be either kappa light chain or lamda light chain.

Preferably, the anti-HLA-DR antibody comprises an IgG1 or a IgG2 heavy chain constant region and a kappa light chain.

The monoclonal antibodies of the present invention can be produced by conventional hybridoma methodology followed by the immunization with HLA-DR antigen. The procedures of hybridoma methodology and immunization are known in the art and also described in detail in Examples. The antibodies can also be produced by using the method of lipid raft immunization, which is disclosed in U.S. Ser. No. 60/331,965, hereby incorporated by reference in its entirety. In particular, the method comprises immunizing an animal with lipid rafts from the interested cancer cells, such as AML cells, creating hybridomas from the immunized animal; screening the hybridomas, and purifying and identifying the hybridoma antibodies (see more details in U.S. Ser. No. 60/331,965). Since HLA-DR is associated with lipid rafts of the leukemia cells, the hybridoma (monoclonal) antibodies against HLA-DR can be produced by lipid raft immunization.

The present invention also includes genetically altered antibodies that are functionally equivalent to the above-described antibodies. Modified antibodies providing improved stability and/or therapeutic efficacy are preferred. Examples of modified antibodies include those with conservative substitutions of amino acid residues, and one or more deletions or additions of amino acids which do not significantly deleteriously alter the antigen binding utility. Substitutions can range from changing or modifying one or more amino acid residues to complete redesign of a region as long as the therapeutic utility is maintained. Antibodies of this invention can be can be modified post-translationally (e.g., acetylation, and phosphorylation) or can be modified synthetically (e.g., the attachment of a labeling group). Since the amino acid sequence of the variable regions of the anti-HLA-DR antibody has been disclosed in the present invention, the nucleic acid sequences of the antibody variable regions are readily available to the skilled artisan, and the genetic modification can be achieved by the standard molecular cloning techniques known in the art.

The genetically altered antibodies also include chimeric antibodies that derived from the anti-HLA-DR antibodies.

Preferably, the chimeric antibodies comprise a variable region derived from a mouse or rat and a constant region derived from a human so that the chimeric antibody has a longer half-life and is less immunogenic when administered to a human subject. The method of making chimeric antibodies is known in the art. The variable region amino acid sequences of the light and heavy chain of the exemplary anti-HLA-DR antibodies (K-388 and anti-HLA-DR#4) are disclosed in SEQ ID NO 3 and 6, and in SEQ ID NO 9 and 12. The variable regions of these antibodies can be connected with a constant region of a human IgG to form the desired chimeric antibody.

Preferably, the genetically altered anti-HLR-DR antibodies used in the present invention include humanized version of the antibodies described herein. More preferably, said humanized antibody comprising CDRs of a mouse donor immunoglobulin and heavy chain and light chain frameworks of a human acceptor immunoglobulin. The method of making humanized antibody is disclosed in U.S. Pat. Nos. 5,301,101; 5,585,089; 5,693,762; and 6,180,370 (each of which is incorporated by reference in its entirety). The amino acid sequences of the CDRs of the exemplary anti-HLA-DR antibodies (K-388 and anti-HLA-DR#4) are disclosed in FIGS. 4, 5, 10 and 11. The CDRs of these antibodies can then be grafted to any selected human frameworks, which are known in the art, to generate the desired humanized antibody.

The fragments of the antibodies disclosed herein, which retain the binding specificity to HLA-DR, are also included in the present invention. Examples include, but are not limited to, the heavy chains, the light chains, and the variable regions as well as the truncated chains (truncated at the carboxyl end), which is particularly useful for immunoscintigraphic procedures. Examples of truncated chains include, but are not limited to, Fab fragment (consisting of the VL, VH, CL and CH1 domains); The Fd fragment (consisting of the VH and CH1 domains); The Fv (consisting of VL and VH domains of a single arm of an antibody); dab fragment (consisting of a VH domain); isolated CDR regions, F(ab') fragment, a bivalent fragment (comprising two Fab fragments linked by a disulphide bridge at the hinge region). The truncated chains can be produced by conventional biochemistry techniques, such as enzyme cleavage, or recombinant DNA techniques, each of which is known in the art.

The variable region of the antibodies and its humanized version of the present invention may be fused to functional regions from other genes (e.g., enzymes, U.S. Pat. No. 5,004,692, which is incorporated by reference in its entirety) to produce fusion proteins (e.g., immunotoxins) or conjugates having novel properties. When used therapeutically, the antibodies disclosed herein may be used in unmodified form or may be modified with an effector moiety that delivers a toxic effect, such as a drug, cytotoxin (preferably, a protein cytotoxin or a Fe domain of the monoclonal antibodies), radionuclide, etc (see, e.g., U.S. Pat. No. 6,086,900, which is incorporated hereby in its entirety.

Conjugates that are immunotoxins including conventional antibodies have been widely described in the art. The toxins may be coupled to the antibodies by conventional coupling techniques or immunotoxins containing protein toxin portions can be produced as fusion proteins. The conjugates of the present invention can be used in a corresponding way to obtain such immunotoxins. Illustrative of such immunotoxins are those described by Byers, B. S. et al. Seminars Cell Biol 2:59–70 (1991) and by Fanger, M. W. et al. Immunol Today 12:51–54 (1991). (See, generally, "Chimeric Toxins," Olsnes and Phil, Pharmac. Ther., 25, 355–381 (1982), and "Monoclonal Antibodies for Cancer Detection and Therapy," eds. Baldwin and Byers, pp. 159–179, 224–266, Academic Press (1985), The present invention provides a method of inducing apoptosis of tumor cells comprising contacting said tumor cells with the anti-HLA-DR antibodies or antibody fragments described herein. The antibodies of the present invention induce apoptosis of the cells selected from the group consisting of myelomonocytic leukemia cells, Burkitts lymphoma cells, non-Hodgkin's lymphoma cells, acute myelocytic leukemia cells, and melanoma. Preferably, the anti-HLA-DR antibodies of the present invention induce apoptosis of AML cells (acute myelocytic leukemia cells), more preferably, KG-1 cells, THP-1 cells. Preferably, the anti-HLA-DR antibodies of the present invention induce apoptosis of B cells, such as Raji or Daudi cells. Preferably the anti-HLA-DR antibodies of the present invention induce apoptosis of melanoma cells, such as C32 and HT-144 cells. Preferably, the monoclonal antibody induces apoptosis by more than 35%. More preferably, the monoclonal antibody induces apoptosis of these cells by more than 50%.

The present invention comprises a pharmaceutical composition comprising the anti-HLA-DR antibodies, antibody fragments or antibody conjugates described herein and a pharmaceutical carrier.

The present invention also provides a method of treating leukemia, lymphomas or solid tumor in a subject in need of the treating comprising administering into a subject in need of the treating the anti-HLA-DR antibodies or antibody fragments described herein in a pharmaceutically effective amount. Preferably, the anti-HLA-DR antibodies can be used for the treatment of Burkitt's lymphoma or various types of leukemia, including, but not limited to, acute leukemias (including acute lymphocytic leukemia (ALL) and acute myelogenous leukemia (AML), chronic leukemias (chronic lymphocytic leukemia (CCL), chronic myelogenous leukemia (CML) or hairy cell leukemia), as well as certain types of solid tumor, including, but not limited to, melanoma or ovarian cancer.

Preferably, pharmaceutical compositions of the present invention are useful for parenteral administration, i.e., subcutaneously, intramuscularly and particularly, intravenously. The compositions for parenteral administration commonly comprise a solution of the antibody or a cocktail thereof dissolved in an acceptable carrier, preferably an aqueous carrier. A variety of aqueous carriers can be used, e.g., water, buffered water, 0.4% saline, 0.3% glycine and the like. These solutions are sterile and generally free of particulate matter. The compositions may contain pharmaceutically acceptable auxiliary substances as required to approximate physiological conditions such as pH adjusting and buffering agents, toxicity adjusting agents and the like, for example sodium acetate, sodium chloride, potassium chloride, calcium chloride, sodium lactate, histidine and arginine. The concentration of the antibodies in these formulations can vary widely, i.e., from less than about 0.01%, usually at least about 0.1% to as much as 5% by weight and are selected primarily based on fluid volumes, and solubilities in accordance with the particular mode of administration selected.

Thus, a typical pharmaceutical composition for injection could be made up to contain 1 ml sterile buffered water, and 1–100 mg of an antibody. A typical composition for intravenous infusion can be made up to contain 250 ml of sterile Ringer's solution, and 10 mg of the inhibitor. Actual methods for preparing parentally administerable compositions are known or apparent to those skilled in the art and are described in more detail in, for example, Remington's Pharmaceutical Science (15th Ed., Mack Publishing Company, Easton, Pa., 1980), which is incorporated herein by reference.

The antibodies of this invention can be frozen or lyophilized for storage and reconstituted in a suitable carrier prior to use depending on the physical characteristics of the inhibitors. This technique has been shown to be effective with conventional antibodies and art-known lyophilization and reconstitution techniques can be employed.

For the purpose of treatment of disease, the appropriate dosage of the above inhibitors will depend on the severity and course of disease, the patient's clinical history and response, the toxicity of the inhibitors, and the discretion of the attending physician. The inhibitors are suitably administered to the patient at one time or over a series of treatments. The initial candidate dosage may be administered to a patient. The proper dosage and treatment regime can be established by monitoring the progress of therapy using conventional techniques known to the people skilled of the art.

The amount of active ingredients that may be combined with the carrier materials to produce a single dosage form will vary depending upon the host treated and the particular mode of administration. It will be understood, however, that the specific dose level for any particular patient will depend upon a variety of factors, including the activity of the specific inhibitor employed, the age, body weight, general health, sex, diet, time of administration, route of administration, and rate of excretion, drug combination and the severity of the particular disease undergoing therapy, and can be determined by those skilled in the art.

The compositions can be administered for prophylactic and/or therapeutic treatments, comprising preventing, inhibiting, and reversing cancer cell proliferation, or inducing the apoptosis of the cancer cells. An amount adequate to accomplish the desired effect without toxic effect is defined as a "pharmaceutically effective amount" and will generally range from about 0.01 to about 100 mg of antibody per dose. Single or multiple administrations can be carried out to achieve the desired therapeutic effect.

Additionally, the compositions can be utilized alone in substantially pure form, or together with chemotherapeutic agents, as are known to those of skill in the art (see, e.g., Cancer: Principles and Practice of Oncology, $5^{th}$ ed., Devita et al., Lippincott-Ravel Publishers, 1997). Other therapies that may be used in conjunction with treatment with the antibodies include administration of antisense nucleic acid molecules or biologicals, such as additional therapeutic antibodies, as well as radiation and/or surgery. Thus, the treatment of the present invention is formulated in a manner allowing it to be administered serially or in combination with another agent for the treatment of cancer.

Antibodies disclosed herein are useful in diagnostic and prognostic evaluation of diseases and disorders, particularly cancers associated with HLA-DR expression. At each stage of disease, monoclonal antibodies may be used to improve diagnostic accuracy and facilitate treatment decisions. Labeled monoclonals antibodies can detect abnormal cells at an early stage, because of their expression of tumor antigens. Once cancer is diagnosed, accurate staging is important in deciding on the most appropriate therapy. Later, during follow-up of surgery, rising serum levels of tumor antigens may indicate recurrence before it can be detected by conventional methods.

Methods of diagnosis can be performed in vitro using a cellular sample (e.g., blood sample, lymph node biopsy or tissue) from a patient or can be performed by in vivo imaging.

In particular embodiments, the present invention provides a method of detecting leukemia, lymphoma, or solid tumor in a subject in need of the detecting comprising contacting the anti-HLA-DR antibodies or antibody fragments described herein with lymphocytes, monocytes or certain cancer cells of said subject and detecting presence of HLA-DR in those cells. Preferably, said solid tumor is ovarian cancer, and the presence of HLA-DR in the ovarian or ovarian cancer cells of a patient is detected. Alternatively, the solid tumor is melanoma. The detection will detect the presence of HLA-DR in the melanoma cells of the patients.

The present invention also includes an antibody conjugate wherein the antibodies of the present invention is conjugated to a diagnostic imaging agent. Compositions comprising the antibodies of the present invention can be used to detect HLR-DR antigen, for example, by radioimmunoassay, ELISA, FACS, etc. One or more labeling moieties can be attached to the humanized immunoglobulin. Exemplary labeling moieties include radiopaque dyes, radiocontrast agents, fluorescent molecules, spin-labeled molecules, enzymes, or other labeling moieties of diagnostic value, particularly in radiologic or magnetic resonance imaging techniques.

The antibodies of the present invention may also be employed for the treatment of other types of cancer or neoplasm or malignant tumors found in mammals, including carcinomas and sarcomas. Examples of cancers are cancer of the brain, breast, cervix, bladder, colon, head & neck, kidney, lung, non-small cell lung, melanoma, mesothelioma, ovary, sarcoma, stomach, uterus, and Medulloblastoma. Preferably, the inhibitors may be employed to treat disorders including, but not limited to, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, cervical cancer, endometrial cancer, adrenal cortical cancer, and leukemia.

Though the antibodies of the present invention are primarily concerned with the treatment of human subjects, they may also be employed for the treatment of other mammalian subjects such as dogs and cats for veterinary purposes.

The following examples are offered by way of illustration and not by way of limitation. The disclosure of all citations in the specification is expressly incorporated herein by reference.

EXAMPLES

Example 1

This example describes generation and characterization of anti-KG-1 lipid raft hybridomas.

Materials and Methods a. Lipid Raft Preparation

Lipid rafts were prepared as described in Green et al, *J. Cell Biol.* 146, 673–682 (1999). Briefly, cells ($8.0 \times 10^6$ cells/sample) were lysed in 0.1% vol/vol Brij-58, 20 mM Tris HCl, pH 8.2, 140 mM NaCl, 2 mM EDTA, 25 μg/ml aprotinin, 25 μg/ml leupeptin, and 1 mM phenylmethylsulfonyl fluoride for 10 minutes on ice. Cells were homogenized using 10 strokes of a Dounce homogenizer, then lysed 20 minutes more on ice. The resulting lysate was adjusted to 40% wt/wt sucrose and applied onto a 60% wt/wt sucrose cushion. A sucrose step-gradient consisting of 25% wt/wt sucrose and 5% wt/wt sucrose were layered on top of the lysate. Gradients were centrifuged 18 hours at 170,000×g at 4° C. in a SW55 rotor. Fractions (0.2 ml) were taken from the top of the gradient. Lipid rafts float to the interface of the 25% and 5% sucrose layers (Fractions 7 and 8). The amount of protein in each fraction was determined using the BCA Protein Assay Kit. Protein was concentrated by centrifugation at 2000×g in Vivaspin 6 PES membrane columns (molecular weight cut off=10,000 kDa).

b. Lipid Raft Immunization

Lipid raft proteins (approximately 5 μg) were mixed together with 50 μL Ribi®, and then injected into the foot pad of a BALB/c mouse. Mice were boosted with 50 μL of lipid raft proteins in Ribi® on day 7 and day 14. Three days after the last boost, the mice were sacrificed and the hind leg lymph node was harvested. The lymph node was washed in pre-warmed DMEM and then ground using a Dounce homogenizer. After 5 gentle strokes, the cell suspension was removed into the plastic tube. This process was repeated four more times, each time adding 5 ml of fresh DMEM. The lymphocytes were pooled and washed 3 times in DMEM. The lymphocytes were mixed with the appropriate number of pre-washed fusion partner NS0/BCL-2 (NS0 transfectant expressing the mouse BCL-2 cDNA) to yield ratio of 2–3 lymphocytes for every 1 NS0. The mixture was pelleted and warmed at 37° C. for 1 min. Pre-warmed 50% PEG was slowly added onto the pellet and then cells were centrifuged at 300×g for 3 minutes at room temperature. Five mL DMEM was added and then 10 mL DMEM with 10% FBS and 1% P/S was added. The cells were then centrifuged 5 minutes at 300×g at room temperature. The pellet was resuspended in HAT selection medium (DMEM with 20% fetal bovine serum, 2 mM glutamine, 0.1 mM non-essential amino acids, 1 mM sodium pyruvate, 0.1 mM sodium hypoxanthine, 16 μM thymidine, 20 μM aminopterin, 2× Origen cloning factor, 10 mM HEPES, 50 μM beta-mercaptoethanol, 0.2 units/mL penicillin, 0.2 μg/mL streptomycin) to yield $0.25 \times 10^6$ lymphocytes/mL. Cells were aliquoted into ten 96-well flat bottom plates at 200 μL per well for the selection of hybridomas.

c. Flow Cytometry Screening

Flow cytometry was used to screen hybridoma supernatants for the presence of cell surface binding antibodies. The cells ($2 \times 10^5$) were resuspended in 100 μL ice cold PBS with 10 μL tissue culture supernatant on ice for 1 hour. After extensive washing, cells were incubated with phycoerythrin-conjugated goat antibodies specific for mouse IgG for 30 minutes on ice. Cells were washed again and cell surface bound antibody was detected using a Becton Dickenson FACScan. Additionally, hybridoma supernatants were similarly screened on whole blood to test for specificity. Normal blood cell populations were purified as described from peripheral blood from volunteers (Brown Methods in Cell Biol. 45, 147 (1994)) or purchased from the Stanford Medical School Blood Center (Stanford, Calif.).

d. Apoptosis of Leukemic Cells

Flow cytometry was used to screen hybridoma supernatants for the ability to induce apoptosis of acute myelogenous leukemia cancer cells. KG-1 cells or THP-1 cells ($2 \times 10^5$) were resuspended in 100 μL media with 100 μL tissue culture supernatant for 24 hours at 37° C. Cells were centrifuged and then incubated with FITC-conjugated annexin V and propidium iodide in 10 mM HEPES, pH 7.4, 150 mM NaCl, 0.5 mM KCl, 1 mM $MgCl_2$, 1.8 mM $CaCl_2$ for 15 minutes at room temperature. After extensive washing, cells were analyzed using a Becton Dickenson FACScan. Apoptotic events were considered to be annexin $V^+$ and $PI^{-/+}$. The apoptosis-inducing activity of purified anti-HLA-DR antibodies was similarly determined using KG-1 or THP-1 cells.

c. Flow Cytometry for Cell Line and Blood Cell Reactivities

To determine blood cell reactivities of K8-355, peripheral blood from normal donors was stained with FITC-conjugated K8-355, L227, or L243 for 15 minutes on ice. Red blood cells were removed by the addition of FACS lysing solution (Becton Dickinson catalog # 349202) for 10 minutes at room temperature. After washing, cell surface bound antibody was detected using a Becton Dickenson FACScan.

To determine if K8-355 is a pan-anti-MHC class II antibody, CESS (myelomonocytic leukemia, American Type Culture Collection (ATCC)), Daudi (Burkitts lymphoma, ATCC), KG-1 (acute myelocytic leukemia, ATCC), Raji (Burkitt's lymphoma, ATCC), Ramos (Burkitt's lymphoma, ATCC), RL (non-Hodgkin's lymphoma, ATCC), and THP-1 (acute myelocytic leukemia, ATCC) were analyzed by flow cytometry. In addition, binding of K8-355 was assessed on 9 individual normal donors as described above.

e. Antibody Variable Region Sequences Determination

Total RNA was extracted from approximately $10^7$ hybridoma cells using TRIzol reagent (Life Technologies, Gaithersburg, Md.) and poly(A)+ RNA was isolated with the PolyATract mRNA Isolation System (Promega, Madison, Wis.) according to the suppliers' protocols. Double-stranded cDNA was synthesized using the SMART™RACE cDNA Amplification Kit (Clontech, Palo Alto, Calif.) following the supplier's protocol. The variable region cDNAs for the light and heavy chains were amplified by polymerase chain reaction (PCR) using 3' primers that anneal respectively to the mouse kappa and gamma chain constant regions, and a 5' universal primer provided in the SMART RACE cDNA Amplification Kit. The 5' universal primer for VL has the sequence:

5' GAT GGA TAC AGT TGG TGC AGC-3' (SEQ ID NO: 13), and that for VH has the sequence:

5'-GCC AGT GGA TAG ACA GAT GG-3'. (SEQ ID NO: 14)

For VL PCR, the 3' primer has the sequence:

5'-TATAGAGCTCAAGCTTGGATGGTGGGAAGATGGATACAGTTGGTGC-3' (SEQ ID NO: 15)

with residues 17–46 hybridizing to the mouse Ck region. For VH PCR, the 3' primers have the degenerate sequences:

```
5'-TATAGAGCTCAAGCTTCCAGTGGATAGAC(ACT)GATGGGG(GC)TGT(CT)    (SEQ ID NO: 16)
GTTTTGGC-3'
``` with residues 17–50 hybridizing to mouse gamma chain CH1. The VL and VH cDNAs were subcloned into pCR4Blunt-TOPO vector (Invitrogen, Carlsbad, Calif.) for sequence determination. DNA sequencing was carried out by PCR cycle sequencing reactions with fluorescent dideoxy chain terminators (Applied Biosystems, Foster City, Calif.) according to the manufacturer's instructions. The sequencing reactions were analyzed on a Model 377 DNA Sequencer (Applied Biosystems).

f. Affinity Purification of Antigen

Cells ($5 \times 10^8$) were lysed in 1% vol/vol NP-40, 0.5% wt/vol deoxycholate, 20 mM Tris HCl, pH 8.2, 150 mM NaCl, 1 mM EDTA, 25 µg/ml aprotinin, 25 µg/ml leupeptin, and 1 mM phenylmethylsulfonyl fluoride for 1 hour on ice with frequent mixing. Lysate was centrifuged for 20 minutes at 300×g to remove nuclei and debris. Antigens were purified by standard hybridoma affinity chromatography techniques as described in Hill et al, *J. Immunol.* 152, 2890–2898 (1994).

g N-Terminal Sequencing

Proteins to be sequenced were separated by SDS-PAGE on a 4–20% gradient gel and then electrotransferred onto a PVDF membrane. The membrane was stained for 2 minutes using colloidal Coomassie and then destained in water. The resulting bands were excised and subjected to N-terminal Edman sequencing as described by Miller, *Methods: A Companion to Methods in Enzymology* 6, 315 (1994).

h. Antigen Grouping

Cells ($2 \times 10^7$) were cell surface iodinated as described (Landolfi and Cook, *Mol. Immunol.* 23, 297–309 (1986)). Alternately, cells were cell surface biotinylated with EZ-Link Sulfo-NHS-LC-Biotin per manufacturers protocol (Pierce cat # 21335). Cells were then lysed in 1% NP-40, 0.5% deoxycholate, 50 mM Tris-HCl, pH 7.4, 150 mM NaCl, 2 mM EDTA, 10 µg/ml aprotinin, 10 µg/ml leupeptin, and 1 mM PMSF for 1 hour on ice. Cell lysate was centrifuged at 14,000×g for 5 minutes to remove nuclei and debris. Cell lysate was pre-cleared with rotation by incubation with Gamma Bind Plus Sepharose beads for 2 hours at 4° C. The beads were spun down and the cell lysate was then aliquoted into Eppendorf tubes containing Gamma Bind Plus Sepharose beads that had been pre-incubated with hybridoma supernatant. The tubes were rotated overnight at 4° C. After extensive washing, bound antigen was eluted from the beads by boiling in the presence of 5% wt/vol SDS, 125 mM Tris-HCl, pH 6.8, and 4% vol/vol β-mercaptoethanol, and 50% vol/vol glycerol. Proteins were then subjected to SDS-PAGE. After electrophoresis, the gel was fixed for 30 minutes with 60% $H_2O$/30% methanol/10% acetic acid. The gel was then washed for 30 minutes with water then dried down. The dried gel was put on film (Kodak® Biomax MS® film with appropriate Biomax MS® screen) overnight. For cell surface biotinylated samples, after electrophoresis proteins were electrotransferred onto a PVDF membrane. The membrane was blocked for 1.5 hours at room temperature in Superblock (Pierce cat #37515). The membrane was then incubated with HRP-conjugated avidin in PBS with 1% BSA and 0.5% Tween-20 for 1 hour at room temperature. After extensive washing, the membrane was developed using enhanced chemiluminescence followed by fluorography.

i. HLA-DR Immunization

Human HLA-DR was isolated from Raji cells using an affinity coulmn as described (Kostelny et al, *Int.J. Cancer* 93, 556–565 (2001). The purified HLA-DR (0.34 mg/ml, lot # 5.11.01 by Brett Jorgensen), which contains one a subunit and one β subunit (1D10 antigen), was mixed with equal volume of Ribi adjuvant and injected into the footpads (50 µl of the final mixture per foot-pad) of a BALB/c mouse. Seven days later the mouse was injected into the footpads with HLA-DR and Ribi mixture again. Three days after the last injections, hind leg lymph nodes were isolated to make lymphocytes for hybridoma fusion. The fusion partner used was the mouse myeloma NS0/BCL2. The fusion of NS0/BCL2 and the lymphocytes were performed using polyethylene glycol (PEG) according to standard procedures. After fusion the cells were plated into 96-well plates containing HAT medium for selection of hybridomas. Spent media from hybridomas were screened for binding to HLA-DR-expressing cells by flow cytometry. Staining of HLA-DR-expressing cells was performed using the spent medium of each hybridoma as primary antibody and phycoerythrin (PE)-conjugated goat anti-mouse IgG (cat. # 1030-09, Southern Biotech, Birmingham, Ala.) as secondary antibodies. Hu1D10, and murine monoclonal antibodies L243 (anti-HLA-DR α, ATCC HB-54) and L227 (anti-HLA-DR β, ATCC HB-96) were used as primary antibody controls. The stained cells were analyzed using the FACScan (Becton Dickinson, Milpita, Calif.).

j. Antibody Characterization

The isotype of each hybridoma antibody was determined by using a mouse monoclonal antibody isotyping kit (cat. # 10126-019, Life Technologies, Gaithersburg, Md.). Hybridomas were expanded in Gibco's Hybridoma-SFM (cat. # 12045-076, Life Technologies, Gaithersburg, Md.). Monoclonal antibodies were purified from hybridoma spent media by protein-G affinity chromatography. For Western blot analysis, purified HLA-DR was run on multiple lanes on a 4–20% polyacrylamide gel under non-reducing conditions. The protein bands in the gel were transferred to a nitrocellulose filter. The filter was incubated with different purified anti-HLA-DR antibodies using a Mini-PROTEIN II multi-screen apparatus (cat. # 170-4017, Bio-Rad, Richmond, Calif.), washed, incubated with biotin-conjugated goat anti-mouse IgG, and then with alkaline phosphatase-conjugated streptavidin to develop binding signals with chromogenic substrate. Conjugation of fluorescein-5-isothiocyanate (FITC) to purified antibodies was performed according to established procedures supplied by the manufacturer of the labeling kit (cat. # F-6434, FluoReceptor FITC Labeling Kit, Molecular Probes, Eugene, Oreg.).

k. Apoptosis of Lymphoma Cells

The ability of each anti-HLA-DR antibody to induce apoptosis was determined using Raji cells (lymphoma). Cells ($3 \times 10^5$ cells/ml) in growth medium were incubated with various antibodies concentrations (0–5 µg/ml) at 37° C. for 1 hr. Samples were then stained with FITC-conjugated human annexin and propidium iodide according to conditions recommended by the manufacturer of the Apoptosis Detection Kit (R&D systems, Minneapolis, Minn.). Cell death was measured by two-color flow cytometry. Cells were defined as being apoptotic if they stained with annexin but had intact membranes as indicated by a lack of staining with propidium iodide. Cells were considered necrotic if they stained with both annexin and propidium iodide. Percentage of cell death was calculated as the sum of apoptotic cells and necrotic cells divided by total number of cells analyzed.

l. Flow Cytometry of Solid Tumor Cells

Log phase cancer cells from various cell lines were washed, trypsinized and resuspand in appropriate media to yield $2\times10^5$ cells/ml. Cells were incubated with murine IgG1 (negative control), or anti-HLA-DR antibodies at 10 μg/ml on ice for 30 min. They were washed and stained with phycoerythrin-conjugated goat antibodies specific for mouse IgG for 30 minutes on ice. Cells were then washed again and cell surface bound antibody was detected using a Becton Dickenson FACScan m. Apoptosis of Melanoma Cells Log phase C32 or HT-144 cells were incubated with anti-HLA-DR antibodies at 10 ug/ml for 24 hours. Floating cells and adherent cells (removed by trypsinization) were collected, washed and incubated with FITC-conjugated annexin V and propidium iodide in 10 mM HEPES, pH 7.4, 150 mM NaCl, 0.5 mM KCl, 1 mM $MgCl_2$, 1.8 mM $CaCl_2$ for 15 minutes at room temperature. After extensive washing, cells were analyzed using a Becton Dickenson FACScan. Apoptotic events were considered to be annexin $V^+$ and $PI^{-/+}$.

Results and Discussions

One BALB/c mouse was immunized with a lipid raft preparation from the acute myelogenous leukemia cell line KG-1. After two boosts, lymphocytes were isolated from the mouse lymph nodes and fused with myeloma NS0 cells to generate hybridomas. A total of about 1142 hybridomas were generated and supernatant from each hybridoma was screened by flow cytometry for binding to KG-1. About 392 hybridomas tested positive. As the normal counter part of acute myelogenous leukemic cells are difficult to purify to screen for differentially expressed antigens, we opted to identify those monoclonal antibodies that have a more restricted expression in blood cells and have anti-cancer activity against KG-1. The 392 KG-1-positive hybridomas were screened against a human T cell line Jurkat by flow cytometry to eliminate those that were reactive to T cells. Antibodies from one hundred and four hybridomas that were Jurkat-negative were identified and their supernatants were tested for KG-1 cell death-inducing activity. Antibodies from 36 selected hybridomas that had apoptosis-inducing activity in an overnight assay were retested in various assays for further characterization. These additional assays included one for the antibody's apoptosis-inducing activity in another AML cell line (THP-1) and several for the antibody's binding activity to T cells, red blood cells, platelets, granulocytes, stem cells (CD34+), lymphocytes and monocytes by flow cytometry. A flow chart of how these 36 anti-KG-1 hybridomas were selected is shown in FIG. 1. The reactivity profiles of these 36 anti-KG-1 hybridomas were summarized in Table 1.

Figure 3A:
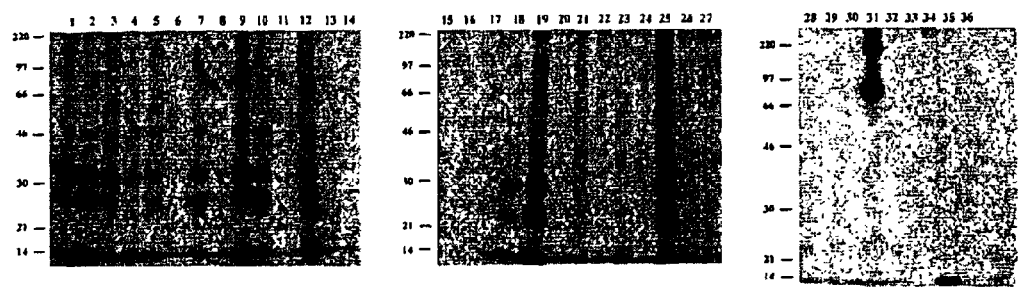
FIG. 3. Antigen grouping by immunoprecipitation. (A). $^{125}$I labeled KG-1 lysate was incubated individually with 36 hybridoma supernatants (see Table 4). Antibody-antigen complexes were captured by Gamma Bind Plus Sepharose and analyzed by SDS-PAGE. Lane 1, K1-34; Lane 2, K1-47; Lane 3, K1-79; Lane 4, K1-95; Lane 5, K1-97; Lane 6, K2-109; Lane 7, K2-124; Lane 8, K2-127; Lane 9, K2-167; Lane 10, K5-37; Lane 11, K5-71; Lane 12, K6-98; Lane 13, K6-103; Lane 14, K6-114; Lane 15, K6-121, Lane 16, K6-149. Lane 17, K6-150; Lane 18, K6-175; Lane 19, K6-179; Lane 20, K7-196; Lane 21, K7-270; Lane 22, K7-275; Lane 23, K8-335; Lane 24, K8-343; Lane 25, K8-355; Lane 26, K8-364; Lane 27, K8-365; Lane 28, K9-3; Lane 29, K9-64; Lane 30, K9-92; Lane 31, K11-230, Lane 32, K11-272, Lane 33, K11-280, Lane 34, K11-282, Lane 35, K12-328, Lane 36, K12-360. Molecular weight standards (MW) are in kD. (B). Biotinylated KG-1 lysate was incubated individually with 15 hybridoma supernatants that failed to identify the molecular weight of their antigens in the experiment shown in panel (A). Antibody-antigen complexes were captured by Gamma Bind Plus Sepharose, analyzed by SDS-PAGE. Lane 1, K8-364; Lane 2, K8-365; Lane 3, K9-92; Lane 4, K11-272; Lane 5, 11-280; Lane 6, K6-150; Lane 7, K6-149; Lane 8, K2-109; Lane 9, K2-127; Lane 10, K5-71; Lane 11, K6-103; Lane 12, K6-114; Lane 13, K6-121; Lane 14, K9-64; Lane 15, K7-196. Molecular weight standards (MW) are in kD.
Figure 3B:
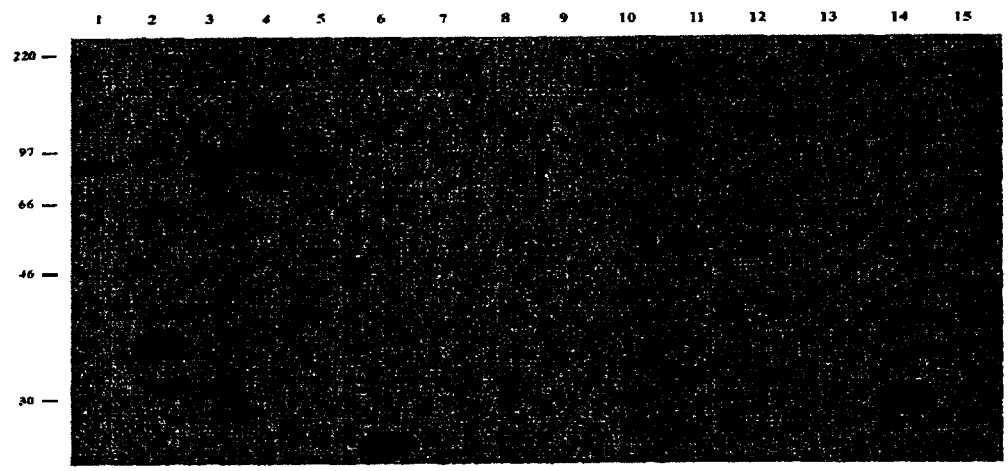

Antigen grouping by immunoprecipitation was used to reduce the number of tumor-associated antigens that need to be characterized. The molecular weights of 24 antigens were determined (FIG. 3) and summarized in Table 1. Fifteen antibodies immunoprecipitated an antigen consisting of two chains of 32 kD and 28 kD. The molecular weights of these two chains resemble those of major histocompatibility complex class II antigen HLA-DR, a predominant antigen in blood cells. We also know by previous experience that some anti-HLA-DR antibodies have potent apoptosis-inducing activity against lymphoma and leukemic cells (Kostelny et al. *Int. J. Cancer* 93, 556–565 (2001)). Using antibody from K8-355 as a representative of this group, we made an affinity column to isolate the antigen from KG-1 cells and confirmed its identity to be HLA-DR by MALDI-TOF peptide profiling.

Figure 6:
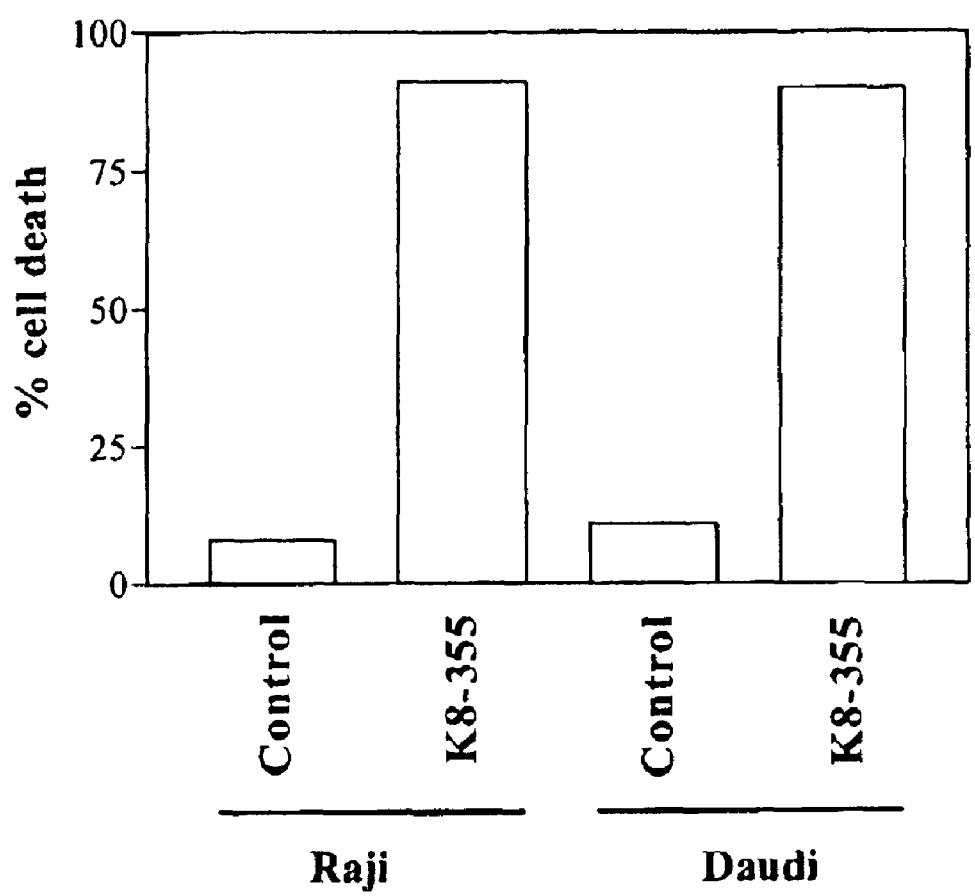
FIG. 6. K8-355 (anti-HLA-DR) induces apoptosis in Raji and Daudi cells. Raji or Daudi cells were treated with K8-355 (5 μg/mL) for 24 hours. Cells were then harvested at the indicated times after the induction of apoptosis and were stained with FITC-conjugated annexin V and propidium iodide. Flow cytometry was used to assess percentage of apoptosis (annexin V$^+$ and propidium iodide$^{-/+}$ cells).

Data indicate that the antibody K8-355 (murine IgG1/ kappa) has a pan-HLA-DR reactivity; it binds to all cells that express HLA-DR in spite of the polymorphic nature of the molecules. The variable regions of the antibody K8-355 have also been determined (FIGS. 4 and 5). In addition to having apoptosis-inducing activity against AML cells such as KG-1 and THP-1, K8-355 also has apoptosis-inducing against the B cell lines Raji and Daudi (FIG. 6).

Figure 8:
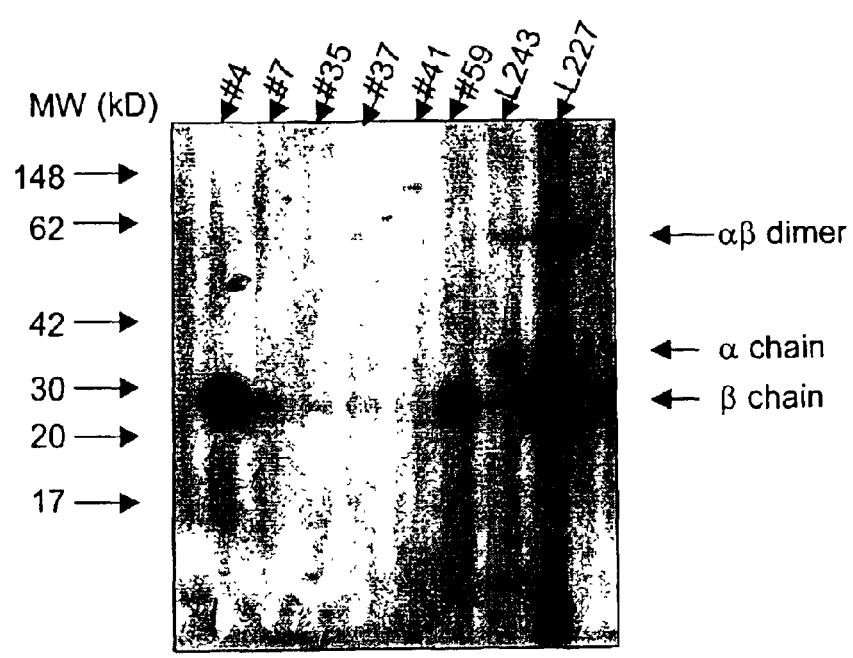
FIG. 8. Western blot analysis of anti-HLA-DR antibodies. Purified HLA-DR protein was run on SDS PAGE and transferred to a nitrocellulose filter. The filter was placed into a Mini-PROTEIN II multiscreen apparatus (cat. # 170-4017, Bio-Rad, Richmond, Calif.) and incubated with purified antibody from hybridomas #4, 7, 35, 37, 41 and 59, as well as L243 and L227 in separate lanes. Antibody binding signals were developed as described in "Material and Methods".

In order to generate more pan-HLA-DR antibodies, a BALB/c mouse was immunized with a purified human HLA-DR antigen and its lymphocytes were fused to myeloma cells to generate 75 hybridomas. Spent medium of each hybridoma was first screened for binding to Raji cells by flow cytometry. Sixteen hybridoma, anti-HLA-DR #4, 7, 8, 11, 14, 27, 28, 34, 35, 37, 41, 51, 59, 62, 67, and 69, were strongly positive in this assay (more than 1.5 log shift of mean channel fluorescence). All of them were then tested on a panel of HLA-DR-expressing cell lines to screen pan-HLA-DR binding activity. The cell lines used were lymphoma cell lines Daudi, Ramos, Priess, CESS, and RL, and AML cell line KG-1. Four hybridomas, #14, 62, 67, 69 showed no binding in some cell lines, while six other hybridomas, #7, 11, 14, 27, 28, 34, showed more variable binding to various cell lines. The remaining six hybridomas, #4, 7, 35, 37, 41, and 59 were strongly positive to all cells tested and were expanded as pan-HLA-DR candidates. Screening results are summarized in Table 2. Monoclonal antibodies from the six candidate pan-HLA-DR hybridomas were purified and their isotypes determined. Western Blot analysis was performed to determine the binding specificity of these antibodies. Of the six tested, only #4 and 59 gave positive signals, recognizing the β chain (28 kD) of HLA-DR (FIG. 8). The same chain was also recognized by the pan-HLA-DR-β antibody L227. L243, a pan-HLA-DR-αantibody, recognized the α chain (32 kD) poorly, perhaps due to its poor binding to the denatured antigen. Pan-HLA-DR hybridomas #7, 35, 37, and 41 did not give any signal in the Western Blot analysis. Perhaps, like L243, they could not bind to the denatured antigen either.

Figure 9:
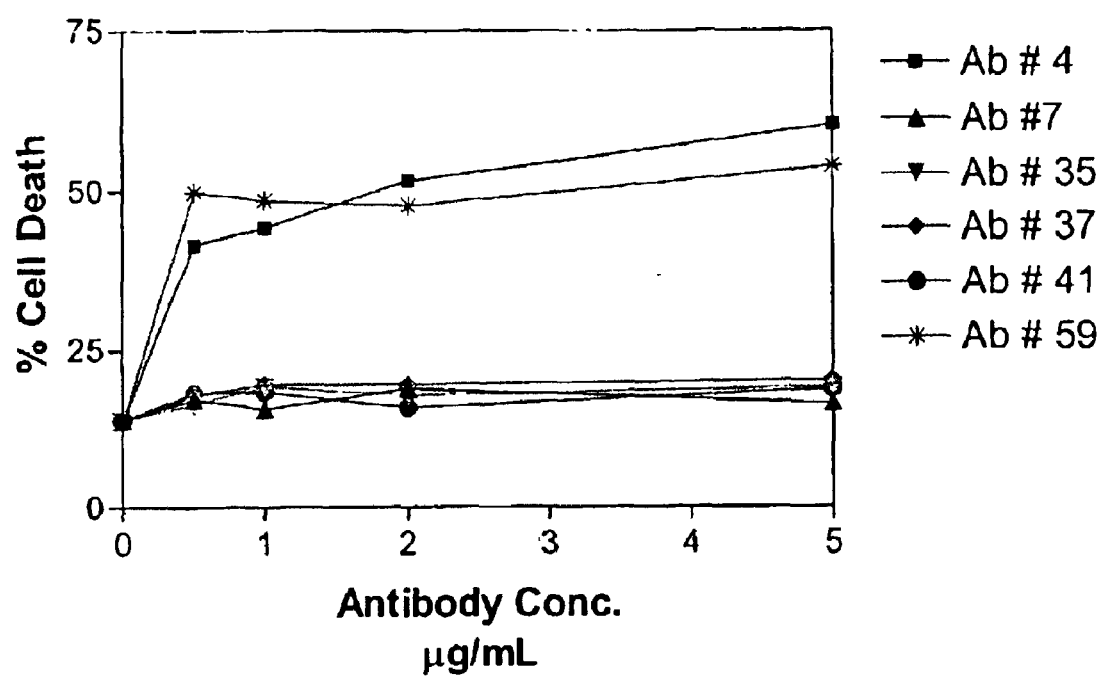
FIG. 9. Apoptosis of Raji cells induced by anti-HLA-DR antibodies. Experimental conditions were described in the "Material and Methods" section using antibodies purified from hybridomas #4, 7, 35, 37, 41 and 59. Percentage of cell death was calculated as the sum of annexin V-positive, propidium iodide-negative population and the annexin V-positive, propidium iodide-positive population divided by the total number of cells analyzed.

Since apoptosis-inducing activity appears to an important mechanism of action of Hu1D10[4], we also tested these six putative pan-HLA-DR antibodies for Raji cell death induction. Results showed in FIG. 9 indicated that both antibodies from hybrioma #4 (IgG2b/kappa) and from #59 (IgG2a/ kappa) were active in inducing cell death in Raji cells. At concentrations 1 μg/ml and above, both antibodies mediated about 30–35% specific cell death, whereas the other four antibodies had only negligible activity. These data established that #4 and 59 are pan-HLA-DR-β antibodies and both have apoptosis inducing activity in B cells. As #59 gave poor antibody yield, #4 was chosen as the additional pan-HLA-DR antibody to be tested in various assays comparing it to K8-355. The monoclonal antibody from the hybridoma #4 is called anti-HLA-DR #4. The variable regions of anti-HLA-DR #4 have also been determined (FIGS. 10 and 11).

Figure 13:
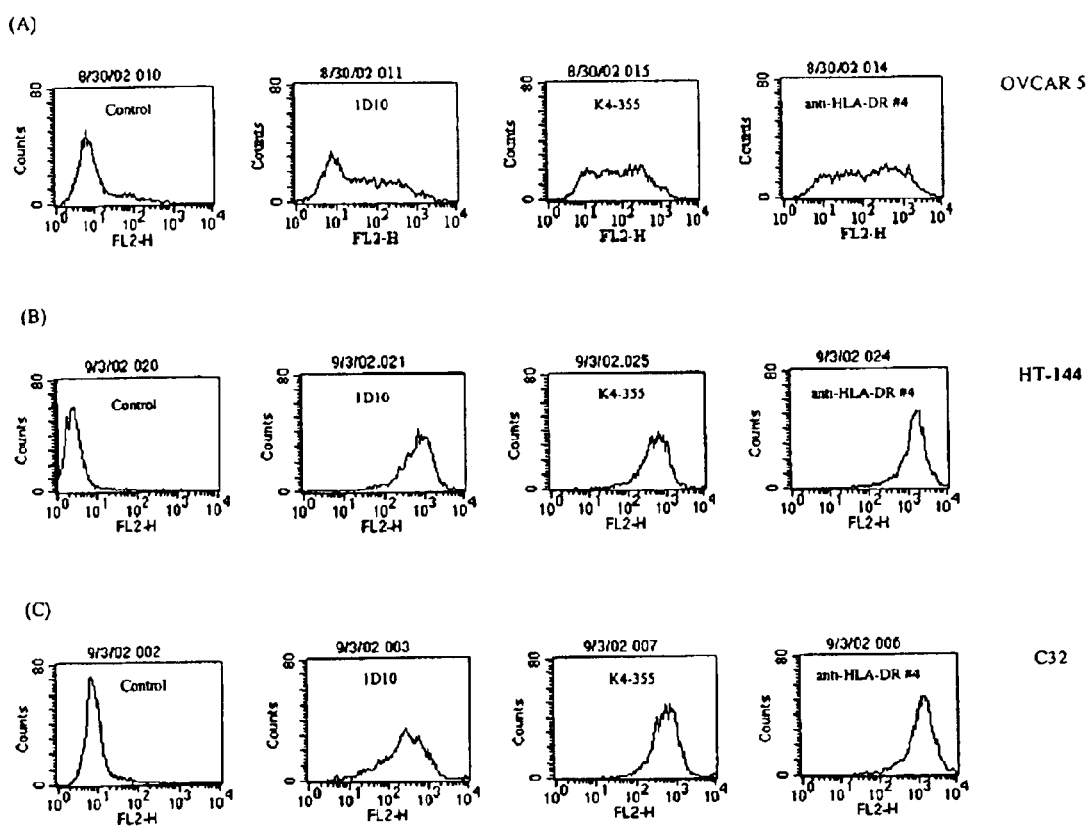
FIG. 13. Reactivity of anti-HLA-DR antibodies for (A) OVCAR-5 (ovarian cancer), (B) HT-144 (melanoma) and (C) C32 (melanoma) cells. Antibodies used were: murine IgG (negative control), the anti-HLA-DR antibodies: ID10, anti-HLA-DR#4, and K8-355 10 μg/mL. The binding of each antibody was developed with a secondary phycoerythrin-conjugated goat antibodies specific for mouse IgG and assayed by flow cytometry.

The reactivity of the two pan-HLA-DR antibodies, K8-355 and anti-HLA-DR #4, to four types of solid tumor cell lines (prostate, ovarian, pancreatic and melanoma) were also tested. As shown in FIG. 12, of the twenty cell lines tested, the reactivity was strongest with two melanoma cell lines, C32 and HT-144, and the ovarian cell line OVCAR-5. The other cell lines that also positive The FACS profiles of these three lines are shown in FIG. 13. The expression of HLA-DR on the surface of OVCAR-5 is heterogeneous. One ovarian cell line (IGROV-1) and two melanoma cell lines (SK-MEL-28 and M14) also have a similar pattern of HLA-DR expression.

The apoptosis-inducing activity of anti-HLA-DR antibodies in the C32 and HT-144 cells were tested. As shown in FIG. 14, in a 24 hour assay, at antibody concentration of 10 $\mu$g/ml, L227 and K8-355 induced about 40% specific cell death in both cell lines. The activity of anti-HLA-DR #4 and 1D10, were modest, at a range of 5–15% specific cell death induction. Taken together, these in vitro data indicate pan-HLA-DR antibodies may have clinical application against leukemia, lymphoma, or certain solid tumor cells.

Example 2

This example describes determining the identity of lipid raft tumor-associated antigens.

Monoclonal antibody that binds to each tumor-associated antigen is to be purified from hybridoma spent medium by protein-G affinity chromatography. The purified monoclonal antibody is then covalently linked to CNBr-activated Sepharose resin to generate an affinity column for a particular antigen. KG-1 cell lysate is to be prepared as in the immunoprecipitation experiment and passed onto the affinity column. Antigen retained in affinity column is eluted and subjected to protein sequence determination by the Edman degradation method. The determined N-terminal sequence is used to search for gene product identity against the Human Genome data bank. Alternatively, the eluted antigen can be subjected to MALDI-TOF peptide-mass profiling and the derived fingerprints be used to search for protein identity against the Human Genome data bank.

Example 3

This example describes inhibition of tumor adhesion and spreading by cell adhesion and migration assay Antibody inhibition of adhesion and spreading is evaluated. Tissue culture 12-well plates were coated 2 hours at room temperature with components of the extracellular matrix, i.e. vitronectin (VN), fibronectin (FN), collagen type I, type III and type IV, laminin (LA), or hyaluronic acid (HA) in Hanks buffered salt solution (HBSS). Plates are blocked for 2 hours with 1% BSA in PBS. Cells are plated in HBSS with 1 mM $CaCl_2$ and 1 mM $MgCl_2$ in the presence or absence of antibody. Cells are allowed to spread for 30 minutes to 2 hours at 37° C. prior to photography.

Inhibition of cancer cell migratory activity of anti-tumor agents is evaluated in a matrigel assay. Membranes with a pore size of 8 $\mu$m were coated with 50 $\mu$l matrigel. The membranes were inserted into 24 well plates that contain medium without supplements. Cancer cells are resuspended in medium with 10% FCS in the presence or absence of antibodies and then seeded on the matrigel coated transwell plates. Plates are incubated for 48 hours at 37° C. Thereafter, cells at the bottom of the chamber are counted using an inverted microscope.

Example 4

This example describes using xenograft models to test the efficacy of the anti-tumor agents.

For solid tumor models, such as Raji or C32 xenograft, six to ten week old male nude NCR nu/nu mice are inoculated subcutaneously in the mid-scapular region with $5 \times 10^6$— Pan-HLA—DR antibodies are given intraperitoneally when tumors reach an average size of 100 $mm^3$, three times per week for 2–3 weeks. Tumors are measured every three to four days with vernier calipers. Tumor volumes are calculated by the formula $\pi/6 \times$(larger diameter)$\times$(smaller diameter)$^2$.

Example 5

This example describes selection of pan-HLA-DR antibodies for cancer therapy based on their antigen expression profiles and anti-cancer activities in vitro.

For solid tumors, monoclonal antibodies against the identified antigens are used to stain by immunohistochemistry normal or neoplastic human tissues to establish the expression profiles of the tumor associated antigens. Valuable tumor-associated antigens should have low or no expression in normal tissues and high expression in cancer cells. To be a good targets for antibody therapy, tumor associated antigens should be differentially expressed in substantial percentage (20% and above) of certain cancer type. Valuable antibodies against these antigens may have anti-cancer activities in vitro. These activities include inhibition of cell proliferation, induction of apoptosis and inhibition of cell migration.

For hematological malignancies, monoclonal antibodies against the identified antigens are used to stain by flow cytometry patient's leukemic cell as well as normal human blood and bone marrow cells. Antigens that are expressed in hematopoietic stem cells (within the CD34-positive population), T cells, platelets, or granulocytes should be excluded because triggering or killing of these cells by antibodies will cause severe toxicity in humans. Antigens of interest may be expressed in B cells, macrophages or monocytes but not in other normal tissues. The ideal tumor-associated antigens are the ones that can be triggered to induce cell death in leukemic cells.

What is claimed is:

1. An isolated antibody that binds to HLA-DR, wherein said antibody comprises a heavy chain having an amino acid sequence of SEQ ID NO: 3.

2. The antibody according to claim 1, wherein said antibody comprises a light chain having an amino acid sequence of SEQ ID NO: 6.

3. The antibody according to claim 2, wherein said antibody is an IgG1 antibody.

4. The antibody according to claim 2, wherein said antibody comprises a kappa light chain.

5. An isolated antibody that binds to HLA-DR, wherein said antibody comprises a heavy chain having an amino acid sequence of SEQ ID NO: 9.

6. The antibody according to claim 5, wherein said antibody comprises a light chain having an amino acid sequence of SEQ ID NO: 12.

7. The antibody according to claim 1, wherein said antibody is an antibody tetramer, Fab fragment, (Fab')$_2$, or Fv.

8. The antibody according to claim 5, wherein said antibody is an antibody tetramer, Fab fragment, (Fab')$_2$, or Fv.

9. An antibody conjugate comprising the antibody according to claim 1.

10. An antibody conjugate comprising the antibody according to claim 5.

11. The antibody conjugate according to claim 9, wherein said antibody is conjugated with a cytotoxin.

12. A pharmaceutical composition comprising the antibody according to claim 1 and a pharmaceutical carrier.

13. A pharmaceutical composition comprising the antibody according to claim 5 and a pharmaceutical carrier.

* * * * *